(12) United States Patent
Colliver et al.

(10) Patent No.: US 7,208,659 B2
(45) Date of Patent: Apr. 24, 2007

(54) PROCESS FOR INCREASING THE FLAVONOID CONTENT OF A PLANT AND PLANTS OBTAINABLE THEREBY

(75) Inventors: Steve Peter Colliver, Bedford (GB); Stephen Glyn Hughes, Exmouth (GB); Shelagh Rachael Muir, Bedford (GB); Adrianus Johannes van Tunen, Wageningen (NL); Martine Elisa Verhoeyen, Bedford (GB)

(73) Assignee: Conopco Inc., Edgewater, NJ (US)

( * ) Notice: Subject to any disclaimer, the term of this patent is extended or adjusted under 35 U.S.C. 154(b) by 272 days.

(21) Appl. No.: 10/136,444

(22) Filed: May 2, 2002

(65) Prior Publication Data

US 2003/0101477 A1 May 29, 2003

(30) Foreign Application Priority Data

May 2, 2001 (EP) .................................. 01304009

(51) Int. Cl.
*C12N 15/29* (2006.01)
*C12N 15/52* (2006.01)
*C12N 15/82* (2006.01)
*A01H 5/00* (2006.01)

(52) U.S. Cl. ................... 800/317.4; 900/298; 900/306; 900/307; 900/317; 800/322; 435/320.1

(58) Field of Classification Search ................ 800/278, 800/298, 306, 307, 317.4, 322; 536/23.1, 536/23.2, 23.6; 435/320.1
See application file for complete search history.

(56) References Cited

U.S. PATENT DOCUMENTS 5,859,329 A 1/1999 Holton et al. ................ 800/205

FOREIGN PATENT DOCUMENTS

| WO | WO 99/37794 | * | 7/1999 |
| WO | WO 00/44909 | | 8/2000 |
| WO | WO 00/53771 | | 9/2000 |

OTHER PUBLICATIONS

Dixon R. et al. Trends in Plant Science, Oct. 1999; vol. 4, No. 10, pp. 1360-1385.*
Pelletier M. et al. Plant Molecular Biology, 1999; vol. 40, pp. 45-54.*
Database EMBL Online, Acc. No. CAA27718, Sep. 12, 1993.
Dixon et al., (1999), Trends in Plant Science, vol. 4, No. 10, pp. 394-400.
Harborne et al., (2000), Phytochemistry, vol. 55, p. 481-504.

* cited by examiner

*Primary Examiner*—Russell P. Kallis
(74) *Attorney, Agent, or Firm*—Morgan, Lewis & Bockius LLP

(57) ABSTRACT

The present invention provides a process for increasing the flavonoid content of a plant wherein said process comprises increasing the activity of chalcone synthase and flavonol synthase therein. The invention further relates to novel plants obtainable by the process of the invention and to food products made therefrom.

19 Claims, 18 Drawing Sheets

Chalcone synthase

Flavonol synthase

A: Peel

B: Flesh

C: Peel

D: Flesh

A: Pericarp

B: Columella

A: Naringenin

B: Kaempferol

A: Naringenin

B: Kaempferol

Figure 1:
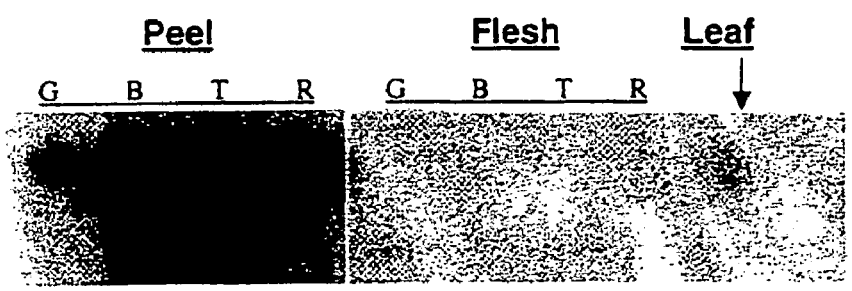
Figure 1:
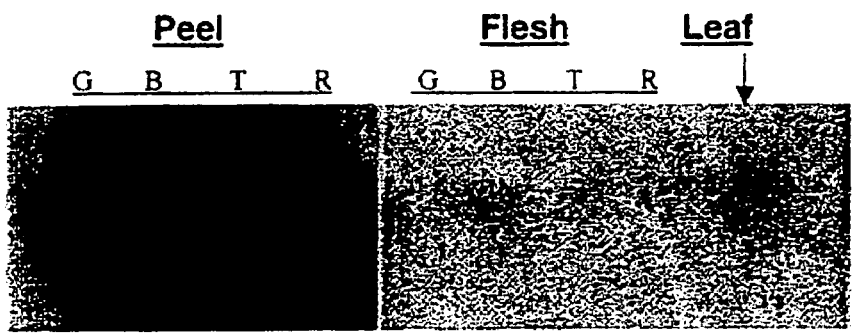

Figure 10: Sequence ID number 1:

```
cttgtcacgtactacataaaaaaaaaaaaataccaaacttttttcaagcaaaaatggtgacagtcgaggagtatcgta
aggcacaacgtgctgaaggtccagccactgtcatggccattggaacagccacacctacaaactgtgttgatcaaagc
acttaccctgattattattttcgtatcactaacagtgagcacaagactgatcttaaggagaaatttaagcgcatgtg
tgaaaaatcaatgattaagaaaaggtacatgcacttaacagaggaaatcttgaaagagaatcctagtatgtgtgaat
acatggcaccttctcttgatgctaggcaagacatagtggtggttgaagtgcccaaacttggcaaagaggcagcccaa
aaggctatcaaggaatggggccagcccaagtccaaaattacccatttggtcttttgcacaactagtggtgtggacat
gcctgggtgtgactatcaactcactaagctacttgggcttcgtccatcggtcaagagcctcatgatgtaccaacaag
gttgctttgctggtggcacggttcttcggttagccaaggacttggcggaaaacaacaagggcgctcgagtccttgtt
gtttgttcagaaatcaccgcggtcaccttccgtgggccaaatgatactcatttggatagtttagttggccaagccct
tttggtgatggggcaggcgcgatcattataggttctgatcaattccaggagtcgagaggcctttgttcgagctcg
tttcagcagcccaaactcttctcccagatagccatggtgctattgatggccatctccgtgaagttgggcttacattc
cacttactcaaagatgttcctgggctgatctcaaaaaatattgagaagagccttgaggaagcatttaaaacctttggg
catttctgattggaactctctattctggattgctcatccaggtgggcctgcaattttggaccaagttgaaataaagt
tgggcctaaagcccgagaaacttaaggctacaaggaatgtgttaagtgactatggtaacatgtcaagtgcttgtgta
ctgtttatttggatgaaatgagaaaggcctcagccaaagaaggtttaggaactactggtgaagggcttgagtgggg
tgttcttttggatttgggcctgggctaacagttgagactgttgtcctccacagtgttgctacttaagtgggttggg
cttatatgaattgaagtgtaattgtttattttgttttcttggggttgaatttatttcgtttgccatgaatgtatttgc
tttagtttgatattgcacttgcaaataaaaataattgtattgaaaactacttaatgaaacaactggacttatctttc
tgtcc
```

Figure 11: Sequence ID number 2:

```
MVTVEEYRKAQRAEGPATVMAIGTATPTNCVDQSTYPDYYFRITNSEHKTDLKEKFKRMCEKSMIKK
RYMHLTEEILKENPSMCEYMAPSLDARQDIVVVEVPKLGKEAAQKAIKEWGQPKSKITHLVFCTTSG
VDMPGCDYQLTKLLGLRPSVKRLMMYQQGCFAGGTVLRLAKDLAENNKGARVLVVCSEITAVTFRGP
NDTHLDSLVGQALFGDGAGAIIIGSDPIPGVERPLFELVSAAQTLLPDSHGAIDGHLREVGLTFHLL
KDVPGLISKNIEKSLEEAFKPLGISDWNSLFWIAHPGGPAILDQVEIKLGLKPEKLKATRNVLSDYG
NMSSACVLFILDEMRKASAKEGLGTTGEGLEWGVLFGFGPGLTVETVVLHSVAT
```

Figure 12: Sequence ID number 3:

```
atgtctcctccagtgtccgttactaaaatgcaggttgagaattacgctttcgcaccgaccgtgaacc
ctgctggttccaccaataccttgttccttgctggtgctgggcatagaggtctggagatagaagggaa
gttgttaagtttacggcgataggtgtgtatctagaagagagtgctattccttttctggccgaaaaat
ggaaaggcaaaaccccccaggagttgactgactcggtcgagttctttagggatgttgttacaggtcc
atttgagaaacttactcgagttactatgatcttgccttgacgggcaagcagtactcggagaaggtg
gcggagaattgtgttgcgcattggaaggggataggaacgtatactgatgatgagggtcgtgccattg
agaagtttctagatgttttccggagtgaaacttttccacctggtgcttccatcatgttactcaatc
accctagggttgttgacgattagcttcgctaaagatgattcagtaactggcactgcgaatgctgtt
atagagaacaagcagttgtctgaagcagtgctggaatcaataattgggaagcatggagtttctcctg
cggcaaagtgtagtgtcgctgaaagagtagcggaactgctcaaaaagagctatgctgaagaggcatc
tgttttggaaaaccggagaccgagaaatctactattccagtgattggagtctagttt
```

Figure 13: Sequence ID number 4:

MSPPVSVTKMQVENYAFAPTVNPAGSTNTLFLAGAGHRGLEIEGKFVKFTAIGVYLEESAIPFLAEK
WKGKTPQELTDSVEFFRDVVTGPFEKFTRVTMILPLTGKQYSEKVAENCVAHWKGIGTYTDDEGRAI
EKFLDVFRSETFPPGASIMFTQSPLGLLTISFAKDDSVTGTANAVIENKQLSEAVLESIIGKHGVSP
AAKCSVAERVAELLKKSYAEEASVFGKPETEKSTIPVIGV

Figure 14: Sequence ID number 5:

gatccacaatggctattccaagagtgacaccttcaacattaacagcattagcagaagaaaagaccct
tcaaacaagtttcattagggatgaagatgaacgtccaaaagtggcttacaaccaattcagcaatgag
atcccaattatctcgttagagggcattgatgatgaaactggtaaaagagctgaaatatgtgacaaga
ttgttaaggcatgtgaagattggggcgttttcaagttgtggatcatggggttgatgctgaagttat
ttcccaaatgacaacttttgctaaagaattctttgctttgcctcctgaggaaaagctgcggtttgac
atgtctggtggcaagaaaggtggatttattgtctctagccatctacagggtgaagtggtccaagatt
ggcgtgaaattgtgacctacttttcgtacccaacaagggcaagagactactctagatggccagacaa
accagaaggatggatagctgtgactcagaaatatagtgaaaagttaatggagttagcttgcaagtta
ttggatgtcctatcagaggctatgggcttggagaaggaggccttaaccaaggcatgtgtggatatgg
accaaaaagtggttgtcaattttttacccaaagtgtcctgagcctgaccttaccttggactgaaaag
acacactgatccaggaaccatcactctcttgttacaagaccaagttggtgggcttcaagctactaaa
gataatggcaaaacttggatcactgttcagcctgttgaaggtgcttttgttgtcaatcttggtgacc
acggtcatttttttgagcaatggacggttcaagaatgctgatcatcaagcagtggtgaactcaaatag
cagcaggttatcgatagccacgtttcagaatccggcaccagaggcgatagtgtatccattgaaaatt
agggaaggagagaagtcaataatggatgagcccataacatttgcagaaatgtacagaaggaaaatga
gcaaggatttagaacttgctaggctcaagaagcaggccaaggagcagcagttacaagctgaagttgc
tgctgagaaggctaagttggagtccaagcccattgaggaaattcttgcttaaattttacatttttta
gcatatttattatattatatgatgaaaaatgatcctcctacctactgttgtaatatctgaatcgg Figure 15: Sequence ID number 6:

MAIPRVTPSTLTALAEEKTLQTSFIRDEDERPKVAYNQFSNEIPIISLEGIDDETGKRAEICDKIVK
ACEDWGVFQVVDHGVDAEVISQMTTFAKEFFALPPEEKLRFDMSGGKKGGFIVSSHLQGEVVQDWRE
IVTYFSYPTRARDYSRWPDKPEGWIAVTQKYSEKLMELACKLLDVLSEAMGLEKEALTKACVDMQK
VVVNFYPKCPEPDLTLGLKRHTDPGTITLLLQDQVGGLQATKDNGKTWITVQPVEGAFVVNLGDHGH
FLSNGRFKNADHQAVVNSNSSRLSIATFQNPAPEAIVYPLKIREGEKSIMDEPITFAEMYRRKMSKD
LELARLKKQAKEQQLQAEVAAEKAKLESKPIEEILA

Figure 16: Sequence ID number 7:

gatccagagggcctaacttctgtatagacaaagaaaaaagaaaagaaaatgaaaacagctcaaggt
gtcagtgcaaccctaacaatggaagtggcaagagtacaagcaatagcatcgttaagcaagtgcatgg
acacaattccatcagagtacattaggtccgagaatgagcaaccagcagccacaaccctgcatggggt
agttcttcaagtgccagtgattgacctacgtgaccctgatgagaacaagatggtgaagctcatagct
gatgctagcaaagagtgggggatattccaactgatcaaccatggcattcctgatgaggctatcgcgg
atttacagaaagtagggaaagagttctttgaacatgttccacaggaggagaaagagctgattgccaa
gactccaggatcaaacgacattgaaggctatggaacttctctgcagaaggaagtggaaggcaagaaa
ggttgggtggatcatttgttccataagatttggcctccttctgccgtcaactatcgttattggccta
aaaaccctccttcatacagggaagcaaacgaagaatatggaaagaggatgcgagaagttgtagacag
aatttttaagagcttgtctcttgggcttgggcttgaaggccatgaaatgatagaggcagctggtggt
gatgagatagtttacttgttgaagatcaactattccaccatgcccaaggcccgatttggctcttg
gtgttgtggcccatacggacatgtcatatatcaccattcttgtcccaaatgaagtccaaggcctcca
agtgttcaaggatggccattggtatgatgtcaagtacataccaaatgccttaattgtccatattggt
gaccaagttgagattcttagcaatggcaaatacaagagtgtataccataggacaacggtgaacaagg
acaagacaagaatgtcatggccggttttcttggagccccgtcagagcatgaagttgggccaattcc
taagctgcttagtgaggccaacccacccaaattcaagaccaagaagtacaaggattacgtctattgt
aagcttaacaagcttcctcagtgaagaagcacctctatgtatggagcgattagctatatcttcgcga
g Figure 17: Sequence ID number 8:

LLYRQRKKEKKMKTAQGVSATLTMEVARVQAIASLSKCMDTIPSEYIRSENEQPAATTLHGVVLQVP
VIDLRDPDENKMVKLIADASKEWGIFQLINHGIPDEAIADLQKVGKEFFEHVPQEEKELIAKTPGSN
DIEGYGTSLQKEVEGKKGWVDHLFHKIWPPSAVNYRYWPKNPPSYREANEEYGKRMREVVDRIFKSL
SLGLGLEGHEMIEAAGGDEIVYLLKINYYPPCPRPDLALGVVAHTDMSYITILVPNEVQGLQVFKDG
HWYDVKYIPNALIVHIGDQVEILSNGKYKSVYHRTTVNKDKTRMSWPVFLEPPSEHEVGPIPKLLSE
ANPPKFKTKKYKDYVYCKLNKLPQ

SEQUENCE LISTING

<160> NUMBER OF SEQ ID NOS: 45

<210> SEQ ID NO 1
<211> LENGTH: 1391
<212> TYPE: DNA
<213> ORGANISM: Petunia hybrida
<300> PUBLICATION INFORMATION:
<303> JOURNAL: Nucleic Acids Res.
<304> VOLUME: 14
<306> PAGES: 5229-5239
<307> DATE: 1986
<308> DATABASE ACCESSION NUMBER: EMBL/X04080
<309> DATABASE ENTRY DATE: 1993-09-12

<400> SEQUENCE: 1
cttgtcacgt actacataaa aaaaaaaaaa taccaaactt tttcaagcaa aaatggtgac        60
agtcgaggag tatcgtaagg cacaacgtgc tgaaggtcca gccactgtca tggccattgg       120

-continued

```
aacagccaca cctacaaact gtgttgatca aagcacttac cctgattatt attttcgtat    180
cactaacagt gagcacaaga ctgatcttaa ggagaaattt aagcgcatgt gtgaaaaatc    240
aatgattaag aaaaggtaca tgcacttaac agaggaaatc ttgaaagaga atcctagtat    300
gtgtgaatac atggcacctt ctcttgatgc taggcaagac atagtggtgg ttgaagtgcc    360
caaacttggc aaagaggcag cccaaaaggc tatcaaggaa tggggccagc ccaagtccaa    420
aattacccat ttggtctttt gcacaactag tggtgtggac atgcctgggt gtgactatca    480
actcactaag ctacttgggc ttcgtccatc ggtcaagagg ctcatgatgt accaacaagg    540
ttgctttgct ggtggcacgg ttcttcggtt agccaaggac ttggcggaaa acaacaaggg    600
cgctcgagtc cttgttgttt gttcagaaat caccgcggtc accttccgtg gccaaatga    660 tactcatttg datagtttag ttggccaagc ccttttggt gatggggcag cgcgatcat    720 tataggttct gatccaattc caggagtcga gaggcctttg ttcgagctcg tttcagcagc    780
ccaaactctt ctcccagata gccatggtgc tattgatggc catctccgtg aagttgggct    840
tacattccac ttactcaaag atgttcctgg gctgatctca aaaaatattg agaagagcct    900
tgaggaagca tttaaacctt tgggcatttc tgattggaac tctctattct ggattgctca    960
tccaggtggg cctgcaattt tggaccaagt tgaaataaag ttgggcctaa agcccgagaa   1020
acttaaggct acaaggaatg tgttaagtga ctatggtaac atgtcaagtg cttgtgtact   1080
gtttattttg gatgaaatga gaaaggcctc agccaaagaa ggtttaggaa ctactggtga   1140
agggcttgag tggggtgttc tttttggatt tgggcctggg ctaacagttg agactgttgt   1200
cctccacagt gttgctactt aagtgggttg ggcttatatg aattgaagtg taattgttta   1260
ttttgtttct tggggttgaa tttatttcgt ttgccatgaa tgtatttgct ttagtttgat   1320
attgcacttg caaataaaaa taattgtatt gaaaactact taatgaaaca actggactta   1380
tctttctgtc c                                                        1391
```

<210> SEQ ID NO 2
<211> LENGTH: 389
<212> TYPE: PRT
<213> ORGANISM: Petunia hybrida
<300> PUBLICATION INFORMATION:
<303> JOURNAL: Nucleic Acids Res.
<304> VOLUME: 14
<306> PAGES: 5229-5239
<307> DATE: 1986
<308> DATABASE ACCESSION NUMBER: SWISS-PROT/P08894
<309> DATABASE ENTRY DATE: 1993-09-12

<400> SEQUENCE: 2

```
Met Val Thr Val Glu Glu Tyr Arg Lys Ala Gln Arg Ala Glu Gly Pro
  1               5                  10                  15

Ala Thr Val Met Ala Ile Gly Thr Ala Thr Pro Thr Asn Cys Val Asp
             20                  25                  30

Gln Ser Thr Tyr Pro Asp Tyr Tyr Phe Arg Ile Thr Asn Ser Glu His
         35                  40                  45

Lys Thr Asp Leu Lys Glu Lys Phe Lys Arg Met Cys Glu Lys Ser Met
     50                  55                  60

Ile Lys Lys Arg Tyr Met His Leu Thr Glu Glu Ile Leu Lys Glu Asn
 65                  70                  75                  80

Pro Ser Met Cys Glu Tyr Met Ala Pro Ser Leu Asp Ala Arg Gln Asp
                 85                  90                  95

Ile Val Val Glu Val Pro Lys Leu Gly Lys Glu Ala Ala Gln Lys
            100                 105                 110
```

Ala Ile Lys Glu Trp Gly Gln Pro Lys Ser Lys Ile Thr His Leu Val
            115                 120                 125

Phe Cys Thr Thr Ser Gly Val Asp Met Pro Gly Cys Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Asn Asp Thr His Leu Asp Ser
        195                 200                 205

Leu Val Gly Gln Ala Leu Phe Gly Asp Gly Ala Gly Ala Ile Ile Ile
    210                 215                 220

Gly Ser Asp Pro Ile Pro Gly Val Glu Arg Pro Leu Phe Glu Leu Val
225                 230                 235                 240

Ser Ala Ala Gln Thr Leu Leu Pro Asp Ser His Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Glu Glu Ala Phe Lys
        275                 280                 285

Pro Leu Gly Ile Ser Asp Trp Asn Ser Leu Phe Trp Ile Ala His Pro
    290                 295                 300

Gly Gly Pro Ala Ile Leu Asp Gln Val Glu Ile Lys Leu Gly Leu Lys
305                 310                 315                 320

Pro Glu Lys Leu Lys Ala Thr Arg Asn Val Leu Ser Asp Tyr Gly Asn
                325                 330                 335

Met Ser Ser Ala Cys Val Leu Phe Ile Leu Asp Glu Met Arg Lys Ala
            340                 345                 350

Ser Ala Lys Glu Gly Leu Gly Thr Thr Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Ala Thr
385

<210> SEQ ID NO 3
<211> LENGTH: 728
<212> TYPE: DNA
<213> ORGANISM: Petunia hybrida
<300> PUBLICATION INFORMATION:
<303> JOURNAL: EMBO J.
<304> VOLUME: 7
<306> PAGES: 1257-1263
<307> DATE: 1988
<308> DATABASE ACCESSION NUMBER: EMBL/X14589
<309> DATABASE ENTRY DATE: 1993-09-12

<400> SEQUENCE: 3
atgtctcctc cagtgtccgt tactaaaatg caggttgaga attacgcttt cgcaccgacc      60
gtgaaccctg ctggttccac caataccttg ttccttgctg gtgctgggca tagaggtctg     120
gagatagaag ggaagttgtt aagtttacgg cgataggtgt gtatctagaa gagagtgcta     180 ttcctttttct ggccgaaaaa tggaaaggca aaaccccca ggagttgact gactcggtcg     240
agttctttag ggatgttgtt acaggtccat ttgagaaatt tactcgagtt actatgatct     300

```
tgcccttgac gggcaagcag tactcggaga aggtggcgga gaattgtgtt gcgcattgga    360
aggggatagg aacgtatact gatgatgagg gtcgtgccat tgagaagttt ctagatgttt    420
tccggagtga aacttttcca cctggtgctt ccatcatgtt tactcaatca cccctagggt    480
tgttgacgat tagcttcgct aaagatgatt cagtaactgg cactgcgaat gctgttatag    540
agaacaagca gttgtctgaa gcagtgctgg aatcaataat tgggaagcat ggagtttctc    600
ctgcggcaaa gtgtagtgtc gctgaaagag tagcggaact gctcaaaaag agctatgctg    660
aagaggcatc tgttttttgga aaaccggaga ccgagaaatc tactattcca gtgattggag    720
tctagttt                                                             728
```

<210> SEQ ID NO 4
<211> LENGTH: 241
<212> TYPE: PRT
<213> ORGANISM: Petunia hybrida
<300> PUBLICATION INFORMATION:
<303> JOURNAL: EMBO J.
<304> VOLUME: 7
<306> PAGES: 1257-1263
<307> DATE: 1988
<308> DATABASE ACCESSION NUMBER: PIR/S04725
<309> DATABASE ENTRY DATE: 1993-09-12

<400> SEQUENCE: 4

```
Met Ser Pro Pro Val Ser Val Thr Lys Met Gln Val Glu Asn Tyr Ala
 1               5                  10                  15

Phe Ala Pro Thr Val Asn Pro Ala Gly Ser Thr Asn Thr Leu Phe Leu
             20                  25                  30

Ala Gly Ala Gly His Arg Gly Leu Glu Ile Glu Gly Lys Phe Val Lys
         35                  40                  45

Phe Thr Ala Ile Gly Val Tyr Leu Glu Glu Ser Ala Ile Pro Phe Leu
     50                  55                  60

Ala Glu Lys Trp Lys Gly Lys Thr Pro Gln Glu Leu Thr Asp Ser Val
 65                  70                  75                  80

Glu Phe Phe Arg Asp Val Val Thr Gly Pro Phe Glu Lys Phe Thr Arg
                 85                  90                  95

Val Thr Met Ile Leu Pro Leu Thr Gly Lys Gln Tyr Ser Glu Lys Val
            100                 105                 110

Ala Glu Asn Cys Val Ala His Trp Lys Gly Ile Gly Thr Tyr Thr Asp
        115                 120                 125

Asp Glu Gly Arg Ala Ile Glu Lys Phe Leu Asp Val Phe Arg Ser Glu
    130                 135                 140

Thr Phe Pro Pro Gly Ala Ser Ile Met Phe Thr Gln Ser Pro Leu Gly
145                 150                 155                 160

Leu Leu Thr Ile Ser Phe Ala Lys Asp Asp Ser Val Thr Gly Thr Ala
                165                 170                 175

Asn Ala Val Ile Glu Asn Lys Gln Leu Ser Glu Ala Val Leu Glu Ser
            180                 185                 190

Ile Ile Gly Lys His Gly Val Ser Pro Ala Ala Lys Cys Ser Val Ala
        195                 200                 205

Glu Arg Val Ala Glu Leu Leu Lys Lys Ser Tyr Ala Glu Glu Ala Ser
    210                 215                 220

Val Phe Gly Lys Pro Glu Thr Glu Lys Ser Thr Ile Pro Val Ile Gly
225                 230                 235                 240

Val
```

-continued

<210> SEQ ID NO 5
<211> LENGTH: 1204
<212> TYPE: DNA
<213> ORGANISM: Petunia hybrida

<400> SEQUENCE: 5

| | | | | | |
|---|---|---|---|---|---|
| gatccacaat | ggctattcca | agagtgacac | cttcaacatt | aacagcatta | gcagaagaaa | 60 |
| agacccttca | aacaagtttc | attagggatg | aagatgaacg | tccaaaagtg | gcttacaacc | 120 |
| aattcagcaa | tgagatccca | attatctcgt | tagagggcat | tgatgatgaa | actggtaaaa | 180 |
| gagctgaaat | atgtgacaag | attgttaagg | catgtgaaga | ttgggggcgtt | tttcaagttg | 240 |
| tggatcatgg | ggttgatgct | gaagttattt | cccaaatgac | aacttttgct | aaagaattct | 300 |
| ttgctttgcc | tcctgaggaa | aagctgcggt | ttgacatgtc | tggtggcaag | aaaggtggat | 360 |
| ttattgtctc | tagccatcta | cagggtgaag | tggtccaaga | ttggcgtgaa | attgtgacct | 420 |
| acttttcgta | cccaacaagg | gcaagagact | actctagatg | gccagacaaa | ccagaaggat | 480 |
| ggatagctgt | gactcagaaa | tatagtgaaa | agttaatgga | gttagcttgc | aagttattgg | 540 |
| atgtcctatc | agaggctatg | ggcttggaga | aggaggcctt | aaccaaggca | tgtgtggata | 600 |
| tggaccaaaa | agtggttgtc | aattttttacc | caaagtgtcc | tgagcctgac | cttacccttg | 660 |
| gactgaaaag | acacactgat | ccaggaacca | tcactctctt | gttacaagac | caagttggtg | 720 |
| ggcttcaagc | tactaaagat | aatggcaaaa | cttggatcac | tgttcagcct | gttgaaggtg | 780 |
| cttttgttgt | caatcttggt | gaccacggtc | atttttttgag | caatggacgg | ttcaagaatg | 840 |
| ctgatcatca | agcagtggtg | aactcaaata | gcagcaggtt | atcgatagcc | acgtttcaga | 900 |
| atccggcacc | agaggcgata | gtgtatccat | tgaaaattag | ggaaggagag | aagtcaataa | 960 |
| tggatgagcc | cataacattt | gcagaaatgt | acagaaggaa | aatgagcaag | gatttagaac | 1020 |
| ttgctaggct | caagaagcag | gccaaggagc | agcagttaca | agctgaagtt | gctgctgaga | 1080 |
| aggctaagtt | ggagtccaag | cccattgagg | aaattcttgc | ttaaattttta | catttttttag | 1140 |
| catatttatt | atattatatg | atgaaaaatg | atcctcctac | ctactgttgt | aatatctgaa | 1200 |
| tcgg | | | | | 1204 |

<210> SEQ ID NO 6
<211> LENGTH: 371
<212> TYPE: PRT
<213> ORGANISM: Petunia hybrida

<400> SEQUENCE: 6

Met Ala Ile Pro Arg Val Thr Pro Ser Thr Leu Thr Ala Leu Ala Glu
 1               5                  10                  15

Glu Lys Thr Leu Gln Thr Ser Phe Ile Arg Asp Glu Asp Glu Arg Pro
             20                  25                  30

Lys Val Ala Tyr Asn Gln Phe Ser Asn Glu Ile Pro Ile Ile Ser Leu
         35                  40                  45

Glu Gly Ile Asp Asp Glu Thr Gly Lys Arg Ala Glu Ile Cys Asp Lys
     50                  55                  60

Ile Val Lys Ala Cys Glu Asp Trp Gly Val Phe Gln Val Val Asp His
 65                  70                  75                  80

Gly Val Asp Ala Glu Val Ile Ser Gln Met Thr Thr Phe Ala Lys Glu
                 85                  90                  95

Phe Phe Ala Leu Pro Pro Glu Glu Lys Leu Arg Phe Asp Met Ser Gly
            100                 105                 110

-continued

```
Gly Lys Lys Gly Gly Phe Ile Val Ser Ser His Leu Gln Gly Glu Val
            115                 120                 125

Val Gln Asp Trp Arg Glu Ile Val Thr Tyr Phe Ser Tyr Pro Thr Arg
        130                 135                 140

Ala Arg Asp Tyr Ser Arg Trp Pro Asp Lys Pro Glu Gly Trp Ile Ala
145                 150                 155                 160

Val Thr Gln Lys Tyr Ser Glu Lys Leu Met Glu Leu Ala Cys Lys Leu
                165                 170                 175

Leu Asp Val Leu Ser Glu Ala Met Gly Leu Glu Lys Glu Ala Leu Thr
            180                 185                 190

Lys Ala Cys Val Asp Met Asp Gln Lys Val Val Asn Phe Tyr Pro
        195                 200                 205

Lys Cys Pro Glu Pro Asp Leu Thr Leu Gly Leu Lys Arg His Thr Asp
210                 215                 220

Pro Gly Thr Ile Thr Leu Leu Gln Asp Gln Val Gly Gly Leu Gln
225                 230                 235                 240

Ala Thr Lys Asp Asn Gly Lys Thr Trp Ile Thr Val Gln Pro Val Glu
                245                 250                 255

Gly Ala Phe Val Val Asn Leu Gly Asp His Gly His Phe Leu Ser Asn
            260                 265                 270

Gly Arg Phe Lys Asn Ala Asp His Gln Ala Val Asn Ser Asn Ser
        275                 280                 285

Ser Arg Leu Ser Ile Ala Thr Phe Gln Asn Pro Ala Pro Glu Ala Ile
    290                 295                 300

Val Tyr Pro Leu Lys Ile Arg Glu Gly Glu Lys Ser Ile Met Asp Glu
305                 310                 315                 320

Pro Ile Thr Phe Ala Glu Met Tyr Arg Arg Lys Met Ser Lys Asp Leu
                325                 330                 335

Glu Leu Ala Arg Leu Lys Lys Gln Ala Lys Glu Gln Gln Leu Gln Ala
            340                 345                 350

Glu Val Ala Ala Glu Lys Ala Lys Leu Glu Ser Lys Pro Ile Glu Glu
        355                 360                 365

Ile Leu Ala
    370
```

<210> SEQ ID NO 7
<211> LENGTH: 1140
<212> TYPE: DNA
<213> ORGANISM: Petunia hybrida

<400> SEQUENCE: 7

| | | | |
|---|---|---|---|
| gatccagagg gcctaacttc tgtatagaca aagaaaaaaa gaaaagaaaa tgaaaacagc | 60 |
| tcaaggtgtc agtgcaaccc taacaatgga agtggcaaga gtacaagcaa tagcatcgtt | 120 |
| aagcaagtgc atggacacaa ttccatcaga gtacattagg tccgagaatg agcaaccagc | 180 |
| agccacaacc ctgcatgggg tagttcttca gtgccagtg attgacctac gtgaccctga | 240 |
| tgagaacaag atggtgaagc tcatagctga tgctagcaaa gagtgggga tattccaact | 300 |
| gatcaaccat ggcattcctg atgaggctat cgcggattta cagaaagtag ggaaagagtt | 360 |
| ctttgaacat gttccacagg aggagaaaga gctgattgcc aagactccag gatcaaacga | 420 |
| cattgaaggc tatggaactt ctctgcagaa ggaagtggaa ggcaagaaag gttgggtgga | 480 |
| tcatttgttc cataagattt ggcctccttc tgccgtcaac tatcgttatt ggcctaaaaa | 540 |
| ccctccttca tacagggaag caaacgaaga atatggaaag aggatgcgag aagttgtaga | 600 |

-continued

```
cagaattttt aagagcttgt ctcttgggct tgggcttgaa ggccatgaaa tgatagaggc      660
agctggtggt gatgagatag tttacttgtt gaagatcaac tattacccac catgcccaag      720
gcccgatttg gctcttggtg ttgtggccca tacggacatg tcatatatca ccattcttgt      780
cccaaatgaa gtccaaggcc tccaagtgtt caaggatggc cattggtatg atgtcaagta      840
cataccaaat gccttaattg tccatattgg tgaccaagtt gagattctta gcaatggcaa      900
atacaagagt gtataccata ggacaacggt gaacaaggac aagacaagaa tgtcatggcc      960
ggttttcttg gagcccccgt cagagcatga agttgggcca attcctaagc tgcttagtga     1020
ggccaaccca cccaaattca agaccaagaa gtacaaggat tacgtctatt gtaagcttaa     1080
caagcttcct cagtgaagaa gcacctctat gtatggagcg attagctata tcttcgcgag     1140
```

<210> SEQ ID NO 8
<211> LENGTH: 359
<212> TYPE: PRT
<213> ORGANISM: Petunia hybrida

<400> SEQUENCE: 8

```
Leu Leu Tyr Arg Gln Arg Lys Lys Glu Lys Lys Met Lys Thr Ala Gln
  1               5                  10                  15

Gly Val Ser Ala Thr Leu Thr Met Glu Val Ala Arg Val Gln Ala Ile
             20                  25                  30

Ala Ser Leu Ser Lys Cys Met Asp Thr Ile Pro Ser Glu Tyr Ile Arg
         35                  40                  45

Ser Glu Asn Glu Gln Pro Ala Ala Thr Thr Leu His Gly Val Val Leu
     50                  55                  60

Gln Val Pro Val Ile Asp Leu Arg Asp Pro Asp Glu Asn Lys Met Val
 65                  70                  75                  80

Lys Leu Ile Ala Asp Ala Ser Lys Glu Trp Gly Ile Phe Gln Leu Ile
                 85                  90                  95

Asn His Gly Ile Pro Asp Glu Ala Ile Ala Asp Leu Gln Lys Val Gly
            100                 105                 110

Lys Glu Phe Phe Glu His Val Pro Gln Glu Glu Lys Glu Leu Ile Ala
        115                 120                 125

Lys Thr Pro Gly Ser Asn Asp Ile Glu Gly Tyr Gly Thr Ser Leu Gln
    130                 135                 140

Lys Glu Val Glu Gly Lys Lys Gly Trp Val Asp His Leu Phe His Lys
145                 150                 155                 160

Ile Trp Pro Pro Ser Ala Val Asn Tyr Arg Tyr Trp Pro Lys Asn Pro
                165                 170                 175

Pro Ser Tyr Arg Glu Ala Asn Glu Glu Tyr Gly Lys Arg Met Arg Glu
            180                 185                 190

Val Val Asp Arg Ile Phe Lys Ser Leu Ser Leu Gly Leu Gly Leu Glu
        195                 200                 205

Gly His Glu Met Ile Glu Ala Ala Gly Gly Asp Glu Ile Val Tyr Leu
    210                 215                 220

Leu Lys Ile Asn Tyr Tyr Pro Pro Cys Pro Arg Pro Asp Leu Ala Leu
225                 230                 235                 240

Gly Val Val Ala His Thr Asp Met Ser Tyr Ile Thr Ile Leu Val Pro
                245                 250                 255

Asn Glu Val Gln Gly Leu Gln Val Phe Lys Asp Gly His Trp Tyr Asp
            260                 265                 270

Val Lys Tyr Ile Pro Asn Ala Leu Ile Val His Ile Gly Asp Gln Val
        275                 280                 285
```

```
Glu Ile Leu Ser Asn Gly Lys Tyr Lys Ser Val Tyr His Arg Thr Thr
        290                 295                 300

Val Asn Lys Asp Lys Thr Arg Met Ser Trp Pro Val Phe Leu Glu Pro
305                 310                 315                 320

Pro Ser Glu His Glu Val Gly Pro Ile Pro Lys Leu Leu Ser Glu Ala
            325                 330                 335

Asn Pro Pro Lys Phe Lys Thr Lys Tyr Lys Asp Tyr Val Tyr Cys
            340                 345                 350

Lys Leu Asn Lys Leu Pro Gln
        355

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 9
cccatcgatg cgtctagtaa catagatgac                                     30

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 10
caattccagg agtcgagagg                                                20

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 11
agtcccccat ggtacgtcct gtagaaacc                                      29

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 12
cgttttcgtc ggtaatcacc attcc                                          25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 13
gaattcaagc ttgacatccc taat                                           24

<210> SEQ ID NO 14
<211> LENGTH: 23
```

```
<212> TYPE: DNA
<213> ORGANISM: Artificial Sequence
<220> FEATURE:
<223> OTHER INFORMATION: Description of Artificial Sequence:Primer

<400> SEQUENCE: 14
cttttgcact gtgaatgatt aga                                              23

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 15
tcgaccatat cgatgcatg                                                   19

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence:Primer

<400> SEQUENCE: 16
catcgatatg g                                                           11

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 17
taagcggccg cagatctgg                                                   19

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 18
aattccagat ctgcggccgc ttaat                                            25

<210> SEQ ID NO 19
<211> LENGTH: 83
<212> TYPE: DNA
<213> ORGANISM: Artificial Sequence
<220> FEATURE:
<223> OTHER INFORMATION: Description of Artificial Sequence:Primer

<400> SEQUENCE: 19
taaggggtac caccatcgat accgaattct acatgcatgc atggagatct cccaagcttc      60
taagatgcgg ccgctaaaca tgg                                              83

<210> SEQ ID NO 20
<211> LENGTH: 89
<212> TYPE: DNA
<213> ORGANISM: Artificial Sequence
<220> FEATURE:
<223> OTHER INFORMATION: Description of Artificial Sequence:Primer
```

-continued

```
<400> SEQUENCE: 20
cgcgccatgt ttagcggccg catcttagaa gcttgggaga tctccatgca tgcatgtaga    60
attcggtatc gatggtggta ccccttaat                                      89

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence:Primer

<400> SEQUENCE: 21
aattgcaccg gtcg                                                      14

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 22
gatccgaccg                                                           10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 23
tagccatggg                                                           10

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 24
tcgacccatg gctaat                                                    16

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 25
cccgtcgact ttccccgatc gttcaaacat ttggc                               35

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 26
cccggatcca aaatggtga cagtcgagg                                       29
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 27
ccggtcgacg caaatacatt catggcaaac g               31

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 28
ggcggatcca aaaatgtctc ctccagtgtc                 30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 29
cccgtcgacc taaactagac tccaatcact                 30

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 30
cggggatcca gagggcctaa cttctgtata gac             33

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 31
cccgtcgact cgcgaagata tagctaatcg c               31

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 32
ccgggatccg gtcttttgca ctgtgaatg                  29

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:Primer -continued

```
<400> SEQUENCE: 33
ggcggtaccc taatgatatt gttcacg                                          27

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 34
aattgggcgc gccaagcttc cgaattctta attaag                                36

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 35
agctcttaat taagaattcg gaagcttggc gcgccc                                36

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 36
tgtctctagc catctacagg                                                  20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 37
gagttcacca ctgcttgatg a                                                21

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 38
ccggtcgact tcgagtatta tggcattgg                                        29

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 39
aatgatagag gcagctggtg                                                  20

<210> SEQ ID NO 40
<211> LENGTH: 21
```

```
<212> TYPE: DNA
<213> ORGANISM: Artificial Sequence
<220> FEATURE:
<223> OTHER INFORMATION: Description of Artificial Sequence:Primer

<400> SEQUENCE: 40
ggcctcacta agcagcttag g                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 41
gcatcacgca gttcaacgct g                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 42
ccggcaacag gattcaatct t                                              21

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 43
cgcaagaccc ttcctctata taag                                           24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 44
agcggataac aatttcacac agga                                           24

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 45
cttctccgag tactgcttgc c                                              21
```

PROCESS FOR INCREASING THE FLAVONOID CONTENT OF A PLANT AND PLANTS OBTAINABLE THEREBY

FIELD OF THE INVENTION

The present invention relates to the field of improving the nutritional content and more particularly the flavonoid content of plants. The invention provides a process for increasing the flavonoid content of plants and the novel plants derivable therefrom.

BACKGROUND TO THE INVENTION

The flavonoids form a large family of low molecular weight polyphenolic compounds, which occur naturally in plant tissues and include the flavonols, flavones, flavanones, catechins, anthocyanins, isoflavonoids, dihydroflavonols and stilbenes (Haslam (1998), Practical Polyphenolics. From Structure to Molecular Recognition and Physiological Action, Cambridge Univ. Press). More than 4000 flavonoids have been described, most are conjugated to sugar molecules and are commonly located in the upper epidermal layers of leaves (Stewart et al., (2000), J. Agric. Food Chem 48:2663–2669).

The prior art provides increasing evidence that flavonoids, especially flavonols are potentially health-protecting components in the human diet. Dietary flavonols help prevent the development of free-radical derived damage to endothelial cells of the coronary arteries and to the development of atherosclerosis (Vinson et al., (1995) J. Agric. Food Chem. 43:2798–2799).

A positive correlation between the high flavonol/flavone intake and a reduction in coronary heart disease has been reported (Hertog et al., (1993) Lancet, 342:1007–1011 and Hertog et al., (1997) Lancet 349:699). A similar relationship was observed in a Finnish cohort study (Knekt et al., (1996) BMJ 312: 478–481) and in the seven countries study (Hertog et al., (1995) Arch Intern Med 155:381–386).

Flavonoids have also been reported to exhibit anti-inflammatory, anti-allergic and vasodilatory activities in vitro (Cook et al., (1996) Nutrit. Biochem. 7:66–76). Such activity has been attributed in part to their ability to act as antioxidants, capable of scavenging free radicals and preventing free radical production.

It is also noteworthy that flavanones possess significant antioxidant activity. For example, naringenin has been reported to exhibit 1.5 times greater antioxidant activity than the vitamins C or E (Rice-Evans et al., (1997) Trends Plant Sci. 2:152–159). Flavanones have also been implicated in cancer prevention. For example, naringenin has been reported to exhibit an anti-oestrogenic activity (Ruh et al., (1995) Biochem. Pharmacol. 50:1485–1493), and also has been shown to inhibit human breast cancer cell proliferation (So et al., (1996) Nutrition and Cancer 26:167–181).

Flavanones and their glycosides are also considered important determinants of taste. For example, in contrast to many other fruit, the genus Citrus is characterised by a substantial accumulation of flavanone glycosides (Berhow and Smolensky, (1995) Plant Sci. 112:139–147). It is noteworthy that in grapefruit the sour taste results mainly from the accumulation of the bitter flavanone glycoside, naringin (Horowitz and Gentili, (1969) J. Agric. Food Chem. 17:696–700). Naringin comprises the flavanone naringenin and a disaccharide neohesperidoside group attached to the 7 position of the A-ring. It is also noteworthy that on a relative scale of bitterness the 7-β-glucoside compounds are between $1/50^{th}$ to $1/5^{th}$ as bitter as quinine (Horowitz and Gentili, (1969) J. Agric. Food Chem. 17:696–700).

The potential advantages of providing food products with elevated flavonoid levels are therefore clearly established in the art. It would be desirable to produce plants which intrinsically possess, elevated levels of health protecting compounds such as flavonoids in order to develop food products with enhanced health protecting properties. Traditionally, the approach to improving plant varieties has been based on conventional cross-breeding techniques, however these require time for breeding and growing of successive plant generations. More recently, recombinant DNA technology has been applied to the general problem of modifying plant genomes to produce plants with desired phenotypic traits.

The flavonoid biosynthetic pathway is well established and has been widely studied in a number of different plant species (see, for example, Koes et al., BioEssays, 16, (1994), 123–132). Briefly, three molecules of malonyl-CoA are condensed with one molecule of coumaroyl-CoA, catalysed by the enzyme chalcone synthase, to give naringenin chalcone which rapidly isomerises, catalysed by chalcone isomerase, to naringenin. Subsequent hydroxylation of naringenin, catalysed by flavanone 3-hydroxylase, leads to dihydrokaempferol. Dihydrokaempferol itself can be hydroxylated, catalysed by flavanone 3'-hydroxylase or flavanone 3',5'-hydroxylase to produce either dihydroquercetin or dihydromyricetin respectively. All three dihydroflavonols subsequently can be converted to anthocyanins (by the action of dihydroflavonol reductase and flavonoid glucosyltransferase) or alternatively converted to flavonols such as kaempferol, quercetin and myricetin by the action of flavonol synthase.

W00/04175 Unilever discloses a process for increasing the flavonoid content of plants wherein through over-expression of chalcone isomerase the flavonol content of a tomato plant may be increased in the peel of the tomato fruit.

Furthermore it is suggested that over-expression of a chimeric chalcone synthase gene in the Poplar hybrid *Populus tremulexp.alba* may give rise to a increase in the level of flavonoid therein. (Niodescu et al, Acta bot. Gallica, 1996, 143(6), 539–546. In one line flavonoids were located in both cortical and peripheral tissues of the stem. In other lines differences in flavonoid were found to be present in superficial tissues.

WO 99/37794 Unilever, discloses a method whereby the incorporation of different transcription factors into the genome of the plant can be used to alter flavonoid levels through the overexpression of genes encoding enzymes of the flavonoid biosynthetic pathway. No reference to overexpression of any specific gene in the pathway is disclosed. Furthermore, the transformed plants provided by this earlier disclosure have been found not to show an increase in both chalcone synthase and flavonol synthase enzyme activities.

The objective technical problem to be solved by the present invention therefore relates to providing an alternative process for increasing the flavonoid content of plants. More-particularly the problem to be solved by the present invention is directed to providing a process which demonstrates enhanced flavonoid synthesis over alternative processes known in the art, specifically in the flesh tissue of fruit.

It was not known at the time of filing that the over-expression of specific combinations of genes which encode enzymes of the flavonoid biosynthetic pathway may be used to increase the content of flavonoids in a plant. Furthermore there was no hint or suggestion in the disclosure of the prior art that any synergistic effect could result from the over-expression of any selected combination of genes encoding enzymes of the flavonoid biosynthetic pathway, nor that such a synergistic effect could be localised to particular edible tissues of a plant. In particular it was not known at the time of filing that increasing the activities of chalcone synthase and flavonol synthase could bring about such results.

Definition of Terms

The expression "plant" is used to refer to a whole plant or part thereof, a plant cell or group of plant cells. Preferably however the invention is particularly directed at transforming whole plants and the use of the whole plant or significant parts thereof such as leaves, fruit, seeds or tubers.

A "pericarp tissue" is used to refer to the wall of a fruit, developing from the ovary wall after fertilisation has occurred.

A "columella tissue" is used to refer to the central axis of a fruit, including placental tissue.

A "flavonoid" or a "flavanone" or a "flavonol" may suitably be an aglycone or a conjugate thereof, such as a glycoside, or a methly, acyl or sulfate derivate. Moreover quercitin and kaempferol as used herein can be taken to refer to either the aglycon or glycoside forms, wherein analysis of the non-hydrolysed extract achieves the glycoside, whereas analysis of the hydrolysed extract achieves the aglycon.

A "gene" is a DNA sequence encoding a protein, including modified or synthetic DNA sequences or naturally occurring sequences encoding a protein, and excluding the 5' sequence which drives the initiation of transcription.

A "DNA sequence functionally equivalent thereto" is any sequence which encodes a protein which has similar functional properties.

According to another embodiment, a functionally equivalent DNA sequence shows at least 50% identity to the respective DNA sequence. More preferably a functionally equivalent DNA sequence shows at least 60%, more preferred at least 75%, even more preferred at least 80%, even more preferred at least 90%, most preferred 95–100% identity, to the respective DNA sequence.

According to the most preferred embodiment a functionally equivalent DNA sequence shows not more than 5 base pairs difference to the respective DNA sequence, more preferred less than 3, e.g. only 1 or 2 base pairs different.

According to another embodiment a functionally equivalent sequence is preferably capable of hybridising under low stringent (2×SSC, 0.1% SDS at 25° C. for 20 min, Sambrook et al 1986) conditions to the respective sequence.

Preferably an equivalent DNA sequence is capable of transcription and subsequent translation to an amino acid sequence showing at least 50% identity to the amino acid sequence encoded by the respective DNA sequence (DNAStar MegAlign Software Version 4.05 and the Clustal algorithm set to default parameters). More preferred, the amino acid sequence translated from an equivalent DNA sequence translated from an equivalent DNA sequence has at least 60%, more preferred at least 75%, even more preferred at least 80%, even more preferred at least 90%, most preferred 95–100% identity to the amino acid sequence encoded by the respective DNA sequence.

"Breaker" is the ripening stage corresponding to the appearance of the first flush of colour on the green fruit.

"Operably linked to a promoter" means the gene, or DNA sequence, is positioned or connected to a promoter in such a way to ensure its functioning. The promoter is any sequence sufficient to allow the DNA to be transcribed. After the gene and promoter sequences are joined, upon activation of the promoter, the gene will be expressed.

A "construct" is a polynucleotide comprising nucleotide sequences not normally associated with nature.

An "increased" level of flavonoids is used to indicate that the level of flavonoids is preferably at least 4 times higher than in similar untransformed plants, more preferred 5–10, most preferred 10–40 times higher than in similar untransformed plants.

BRIEF DESCRIPTION OF THE INVENTION

It has now been found that the over-expression of a gene combination comprising genes encoding chalcone synthase and flavonol synthase provides a novel process by which the flavonoid content of a plant may be increased. Moreover, it has been demonstrated by way of the present invention that this novel combination exhibits a synergy over and above the effect on flavonoid content of over expressing either gene individually in a plant.

Accordingly it is a first object of the invention to provide a process for increasing the flavonoid content of a plant wherein said process comprises, increasing the activity of chalcone synthase and flavonol synthase therein.

Preferably the process of the invention will achieve increased activity of chalcone synthase and flavonol synthase by the addition to the genome of a plant of one or more nucleotide sequences encoding each of these enzymes.

A first embodiment of the invention is therefore directed to a process as described above wherein said process comprises incorporating into said plant one or more nucleotide sequences encoding a chalcone synthase and one or more nucleotide sequences encoding a flavonol synthase.

It is preferred that said one or more nucleotide sequences encoding each of these enzymes is incorporated into the genome of a plant via a genetic transformation of said plant.

A second embodiment of the invention is therefore said to comprise a process as described above wherein said process comprises the steps;

(i) transforming a plant cell with a gene construct;
(ii) regenerating said plant cell to produce a transformed plant;

wherein said gene construct comprises one or more nucleotide sequences encoding a chalcone synthase and one or more nucleotide sequences encoding a flavonol synthase. Preferably said gene construct comprises nucleotide sequences according to sequence identification numbers 1 and 7 or functional equivalents thereof.

The process of the invention may be applied to increase the flavonoid content of a plant by increasing enzyme activity throughout a plant or, more preferably, by increasing localised enzyme activity in certain tissues, in particular leaves and/or fruits. This localised increase in enzyme activity allows greater improvement in flavonoid content to be achieved in those tissues which normally form the edible parts of the plant while maintaining good viability in the progeny.

A further embodiment therefore comprises a process as described above wherein the flavonoid content of said plant is increased in leaf tissue and/or fruit tissue.

It has been found that the increase in flavonoid content observed in plants modified according to the process outlined above comprises an increase in a plurality of different flavonoid types depending on the nature of the plant tissue in which modified gene expression is occurring. Preferably the increase in flavonoid content in a plant according to the invention comprises an increase in flavanone content and/or an increase in flavonol content.

It is particularly advantageous that the present invention provides a process by which an increase in the flavonoid content of a plant can be achieved by a localised increase in flavanone and/or flavonol content in those tissues which make up the non-peel i.e. flesh component of a fruit. These tissues may typically include pericarp tissue and columella tissue.

Embodiments of the invention therefore comprise a process as disclosed above wherein the flavanone content of said plant is increased in pericarp tissue and further more a process as disclosed above wherein flavanone content of said plant is increased in columella tissue.

It has been shown that the content of the flavanone naringenin may be particularly increased in fruit tissue by way of the disclosed process. Peel, pericarp and columella tissues all showed high levels of naringenin. The pericarp was found to have up to a 290 fold increase over control plants and the columella tissue a 730 fold increase over control plants.

A preferred embodiment of the invention therefore comprises a process as disclosed above wherein said flavanone content comprises naringenin.

It has also been shown that the content of the flavonol kaempferol may be particularly increased in the flesh component of a fruit. The kaempferol content of the pericarp tissue was increased up to 14 fold over the control and the columella tissue an increase of up to 32 fold over control plants.

A further embodiment of the invention therefore comprises a process as disclosed above wherein said flavonol content comprises kaempferol.

It has been shown that the increase flavonoid level observed in those plants of the present invention is not a cummulative effect of the over-expression of CHS and FLS. The observed increase in the flavonoid content is a demonstration of a synergy found to exist in selecting to increase the activities of both chalcone synthase and flavonol synthase in a plant.

The over-expression of the further enzymes, chalcone isomerase or flavanone 3-hydroxylase can be used to further increase the flavonoid.

The invention also relates to a gene construct suitable for the genetic transformation of a plant in accordance with the process described above.

Accordingly, a second object of the invention is to provide a gene construct comprising one or more nucleotide sequence encoding a chalcone synthase and one or more nucleotide sequences encoding a flavonol synthase wherein said nucleotide sequences are operably linked to a promoter.

It is a third object of the invention to provide the use of a construct as previously described in the genetic transformation of a plant.

It is a fourth object of the invention to provide a genetically modified plant with an increased flavonoid content compared to an equivalent unmodified plant, wherein said genetically modified plant is obtainable by a process according to the above description.

Preferably the plants according to the invention are suitable for human consumption. Suitable plants are for example from the Pisum family such as peas, family of Brassicae, such as green cabbage, Brussel sprouts, cauliflower, the family of Phaseolus such as barlotti beans, green beans, kidney beans, the family of Spinacea such as spinach, the family of Solanaceae such as potato and tomato, the family of Daucus, such as carrots, family of Capsicum such as green and red pepper, and the family of Ribesiaceae such as strawberries, blackberries, raspberries, black currant and edible grasses from the family of Gramineae such as maize, and citrus fruit for example from the family of Rutaceae such as lemon, orange, tangerine, or from the apple family. Also preferred oil producing plant such as sunflower, soybean and rape. Also preferred are plants which can form the basis of an infusion such as black tea leaves, green tea leaves, jasmine tea leaves. Also preferred is the tobacco plant.

A particularly preferred plant for use in the method according to the invention is the tomato plant.

The invention also relates to the use of the plant according to the invention or desired parts thereof in the preparation of food products or skin or hair protective products.

DETAILED DESCRIPTION OF THE INVENTION

The present invention as disclosed above has identified that altering a plant to increase the activities of chalcone synthase and flavonol synthase in combination gives rise to a significant increase in the flavonoid content of such a plant.

It has been found that it is possible to increase the level of flavonoids, particularly flavanones and flavonols in tomato fruit and even more surprising in the flesh of a tomato fruit, a tissue that normally contains only trace amounts of flavonoids, thereby producing tomatoes with enhanced nutritional, preservative and flavour characteristics.

The present invention also identifies that increasing the activities of additional enzymes in a plant can be effective in bringing about an increase in the flavonoid content therein. In this respect it is demonstrated that increasing the activities of a group of enzymes comprising chalcone synthase (CHS), chalcone isomerase (CHI), flavanone 3-hydroxylase (F3H) and flavonol synthase (FLS) is effective in increasing the levels of flavonoid in a plant. Preferably this group of enzymes comprises CHS, CHI and FLS as these are believed to be most influential on flavonoid biosyntheses. The advantage of additionally increasing CHI activity is to provide increased flavonol levels in peel tissue as well as flesh tissue, in particular the flavonols quercetin and kaempferol as previously described in WO0/04175 which is incorporated herein by reference. This can be enabled by incorporating into a plant appropriate nucleotide sequences encoding these enzymes, preferably as demonstrated herein, this is accomplished via the route of genetic transformation.

This combination of increased enzyme activities has been shown to further increase the flavonoid content through the flavonol component thereof. More particularly this is reflected as an increase in the content of the flavonols quercetin and/or kaempferol in the peel tissue of a modified plant. Neither the content of quercetin nor kaempferol can be increased in the peel tissues of plants which have been modified to increase CHS alone, FLS alone or CHS and FLS in combination.

By analogy to the demonstrated effect on flavonoid content in tomato fruit tissue under the control of a fruit specific promoter, the process of the invention may be used to increase the level of flavonoids, in particular by increasing the levels of flavanones and flavonols, in other specific tissues of a plant in which flavonoid biosynthesis occurs.

Of particular advantage is to increase flavonoid levels of leaves where these are to be consumed as food products such as spinach and tea, it is advantageous that the level of flavonoids, in particular flavonols are increased in such leaves. For fruit-bearing plants such as tomato, strawberry, apple etc it is advantageous that the level of flavonoids, in particular the level of flavanones and/or flavonols, is increased in the fruit. For plants with edible flowers e.g. broccolli and cauliflower it is advantageous that the level of flavonoids, in particular the level of flavanones and/or flavonols, is increased in the flower. For plants with edible stems such as asparagus it is advantageous that the level of flavonoids, in particular the level of flavanones and/or flavonols, is increased in the stem. For edible seeds, such as peas, sunflower seed or rapeseed it is advantageous that the level of flavonoids, in particular the level of flavanones and/or flavonols, is increased in the seed etc. Typically the type and choice of one or more of the regulatory sequences for the genes encoding the biosynthetic enzymes can provide the desired increase in specific parts of the plants.

For the preparation of food products from plants according to the invention the desired parts of the plant with the altered level of flavonoids may be harvested and further processed for consumption or storage. For example, leaves of a spinach plant, modified according to the invention may be subsequently blanched, chopped, frozen and packaged for storage. Similarly tea leaves can be processed to provide tea with an enhanced flavonoid content.

Seeds such as peas may be harvested and further processed e.g. blanching and freezing into pea products. In addition, comminuted products may be made e.g. pea soup. Other seeds e.g oil seeds such as sunflower seed or soy-bean may be used for the extraction of oil.

Plant flowers such as broccoli or cauliflower may be harvested and further processed e.g. to prepare frozen vegetables or soup. Also stems such as asparagus may be harvested and further processed e.g. to produce asparagus soup.

A particularly preferred embodiment of the invention relates to the fruits especially tomatoes with increased levels of flavonoids, particularly flavanones and flavonols. These tomatoes may be harvested and eaten fresh. For fresh consumption suitable tomato varieties for modification in accordance with the present invention include the salad variety Ailsa Craig. Alternatively, the tomatoes may be used in the preparation of food products. Also heat-treatment may be applied, for example tomatoes may be used to prepare tomato sauces with tomato as one of the main ingredients such as tomato paste, tomato ketchup, pizza sauce, pasta sauce, salsas, or dressings. Also the tomatoes may be used to prepare products like tomato juice or tomato soups. Tomatoes according to the invention may alternatively be used in the preparation of high flavonoid containing extracts, or at least partially dried and consumed in such a dried form.

The sequence encoding a biosynthetic enzyme for flavonoid biosynthesis may be a genomic or cDNA clone, or a sequence which in proper reading frame encodes an amino acid sequence which is functionally equivalent to the amino acid sequence of the biosynthetic gene encoded by the genomic or cDNA clone. A functional derivative can be characterised by an insertion, deletion or a substitution of one or more bases of the DNA sequence, prepared by known mutagenic techniques such as site-directed mutagenesis or derived from a different species. The functionality can be evaluated by routine screening assays, for example, by assaying the flavonoid content of the resulting transgenic plant.

Gene sequences encoding enzymes for flavonoid biosynthesis for use according to the present invention may suitably be obtained from plants, in particular higher plants as these generally possess a flavonoid biosynthetic pathway.

Genes involved in flavonoid biosynthesis have been isolated from various plant species such as, but not limited to: *Petunia* (see, for example, Van Tunen et al., (1988) EMBO J. 7:1257–1263; Koes et al., (1989) Gene 81:245–257), *Antirrhinum* (see, for example, Grotewald and Peterson (1994) Mol. Gen. Genet., 242:1–8; Sommer and Saedler (1986), Mol. Gen. Genet., 202:429–434) and maize (see, for example, Grotewald and Peterson (1994), Mol. Gen. Genet. 242:1–8).

The *Petunia* plant is a particularly preferred source. Alternatively, equivalent genes could be isolated from plant gene libraries, for example by hybridisation techniques with DNA probes based on known flavonoid biosynthetic genes.

CHS coding sequence highly conserved and number of suitable CHS sequences for the purpose of the present invention are known in the art. Neisbach-Klosgen reported nucleotide similarity higher than 66% and amino acid similarity higher than 80% over the coding regions of CHS isolated from a number of different species (*Antirrhinum, Petroselinum, Zea, Ranunculus, Petunia, Magnolia, Hordeum*). FLS alignment indicate greater than 48% identity at nucleotide and greater than 50% identity at amino acid level from a number of different species (*Petunia, Solanum, Malus, Citrus, Arabidopsis*) which can be suitably used in the present invention.

The gene sequences of interest will be operably linked (that is, positioned to ensure the functioning of) to one or more suitable promoters which allow the DNA to be transcribed. Suitable promoters, which may be homologous or heterologous to the gene (that is, not naturally operably linked to a gene encoding an enzyme for flavonoid biosynthesis), useful for expression in plants are well known in art, as described, for example, in Weising et al., (1988) Ann. Rev. Genetics 22:421–477. Promoters for use according to the invention may be inducible, constitutive, or tissue-specific or have various combinations of such characteristics.

Useful promoters include, but are not limited to constitutive promoters such as carnation etched ring virus (CERV) promoter, cauliflower mosaic virus (CaMV) 35S promoter, or more particularly the enhanced cauliflower mosaic virus promoter, comprising two CaMV 35S promoters in tandem (referred to as a "Double 35S" promoter). These would have the effect of increasing flavonoid levels throughout a plant.

For the purpose of the present invention it is preferred to use a tissue-specific or developmentally regulated promoter instead of a constitutive promoter. A tissue-specific promoter induces or increases expression of the gene(s) for flavonoid biosynthesis in certain desired tissues, preferably without enhancing expression in other, undesired tissues. This has the advantage that the tissue of interest shows the desired flavonoid increase while the possible impact on other plant tissues is minimised, thereby maintaining high viability in the progeny.

Promoters used in over-expression of the biosynthetic enzymes for flavonoid biosynthesis in tomato plants will preferably be tissue specific, especially fruit-specific. Suitable fruit-specific promoters include the tomato E8 promoter (Deikman et al., (1988) EMBO J 7:3315–3320), 2A11 (Van Haaren et al., (1993) Plant Mol Biol 21:625–640), E4 (Cordes et al., (1989) Plant Cell 1:1025–1034) and PG (Bird et al., (1988) Plant Mol Biol 11:651–662; Nicholass et al., (1995) Plant Mol Biol 28:423–435).

It is noteworthy that in these studies sequences encoding CHS and FLS were placed under the control of the tissue-specific tomato E8 promoter. Much larger increases in flavonol accumulation in pericarp and columella tissues may however be achieved, by linking the CHS and FLS transgenes to stronger promoters, such as CaMV35S. This is supported by ectopic expression of CHI under the control of the relatively 'weak' granule bound starch synthase promoter from potato resulted in only a 4-fold increase in flavonol accumulation in peel tissue compared with an up to 78-fold increase observed when CHI was introduced under the control of the strong CaMV35S promoter (data unpublished).

Accordingly, the invention provides in a further aspect a gene construct in the form of an expression cassette comprising as operably linked components in the 5'-3' direction of transcription, one or more units each comprising a suitable promoter in a plant cell, a plurality of nucleotide sequences selected from the group comprising sequences encoding a CHS, CHI and FLS for flavonoid biosynthesis and a suitable transcriptional and translational termination regulatory region. More preferably said group comprising sequences encoding CHS and FLS.

The promoter and termination regulatory regions will be functional in the host plant cell and may be heterologous or homologous to the plant cell and the gene. Suitable promoters which may be used are described above.

The termination regulatory region may be derived from the 3' region of the gene from which the promoter was obtained or from another gene. Suitable termination regions, which may be used, are well known in the art and include *Agrobacterium tumefaciens* nopaline synthase terminator (Tnos), *Agrobacterium tumefaciens* mannopine synthase terminator (Tmas), the rubisco small subunit terminator (TrbcS) and the CaMV 35S terminator (T35S). Particularly preferred termination regions for use according to the invention include the Tnos and TrbcS termination regions.

Such gene constructs may suitably be screened for activity by transformation into a host plant via *Agrobacterium tumefaciens* co-transformation and screening for flavonoid levels.

Conveniently, the expression cassette according to the invention may be prepared by cloning the individual promoter/gene/terminator units into a suitable cloning vector. Suitable cloning vectors are well known in the art, including such vectors as pUC (Norrander et al., (1983) Gene 26:101–106), pEMBL (Dente et al., (1983) Nucleic Acids Research 11:1645–1699), pBLUESCRIPT (available from Stratagene), pGEM (available from Promega) and pBR322 (Bolivar et al., (1977) Gene 2:95–113). Particularly useful cloning vectors are those based on the pUC series. The cloning vector allows the DNA to be amplified or manipulated, for example by joining sequences. The cloning sites are preferably in the form of a polylinker, that is a sequence containing multiple adjacent restriction sites, so as to allow flexibility in cloning.

Preferably the DNA construct according to the invention is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., Cloning Vectors. A laboratory manual, Elsevier, Amsterdam (1986). Particularly suitable vectors include the Ti plasmid vectors.

Transformation techniques for introducing the DNA constructs according to the invention into host cells are well known in the art and include such methods as microinjection, using polyethylene glycol, electroporation, or high velocity ballistic penetration. A preferred method for use according to the present invention relies on *Agrobacterium tumefaciens* mediated co-transformation.

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assay within the knowledge of the person skilled in the art may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved flavonoid levels may be propagated and crossed to produce homozygous lines. Such plants produce seeds containing the genes for the introduced trait and can be grown to produce plants that will produce the selected phenotype.

It is recognised that the overexpression of genes encoding biosynthetic enzymes for flavonoid biosynthesis according to the process of the invention may result in the accumulation of both anthocyanins and flavonoids other than anthocyanins, particularly if the biosynthetic enzymes operate at a position along the flavonoid biosynthesis pathway before the respective flavonol and anthocyanln pathways diverge. This may be undesirable as the formation of anthocyanins not only results in the production of aesthetically unpleasing purple coloured fruits, but may also limit the production of flavonols.

In a further embodiment, this may be avoided by blocking the route to expression of anthocyanins for example by an additional step comprising antisense suppression of dihydroflavonol reductase (DFR), the enzyme catalysing the final step in the production of anthocyanins. Alternatively, biosynthetic enzymes may be overexpressed in a mutant line, such as a tomato line which is deficient in DFR activity, for example, the anthocyanin without (aw) mutant which is described by Goldsbrough et al., (1994) Plant Physiol 105: 491–496.

The present invention may be more fully understood by reference to the accompanying drawings in which:

FIG. 1: Northern analysis of tomato fruit harvested at different developmental stages, denoted as: green (G), breaker (B), turning (T) and red (R), and separated into peel and flesh. Leaves were harvested from young tomato plants. RNA was isolated from the samples, separated on formaldehyde agarose gels, blotted and hybridised with *Petunia hybrida* chs-a (chalcone synthase) or fls (flavonol synthase) probes.

Figure 2A:
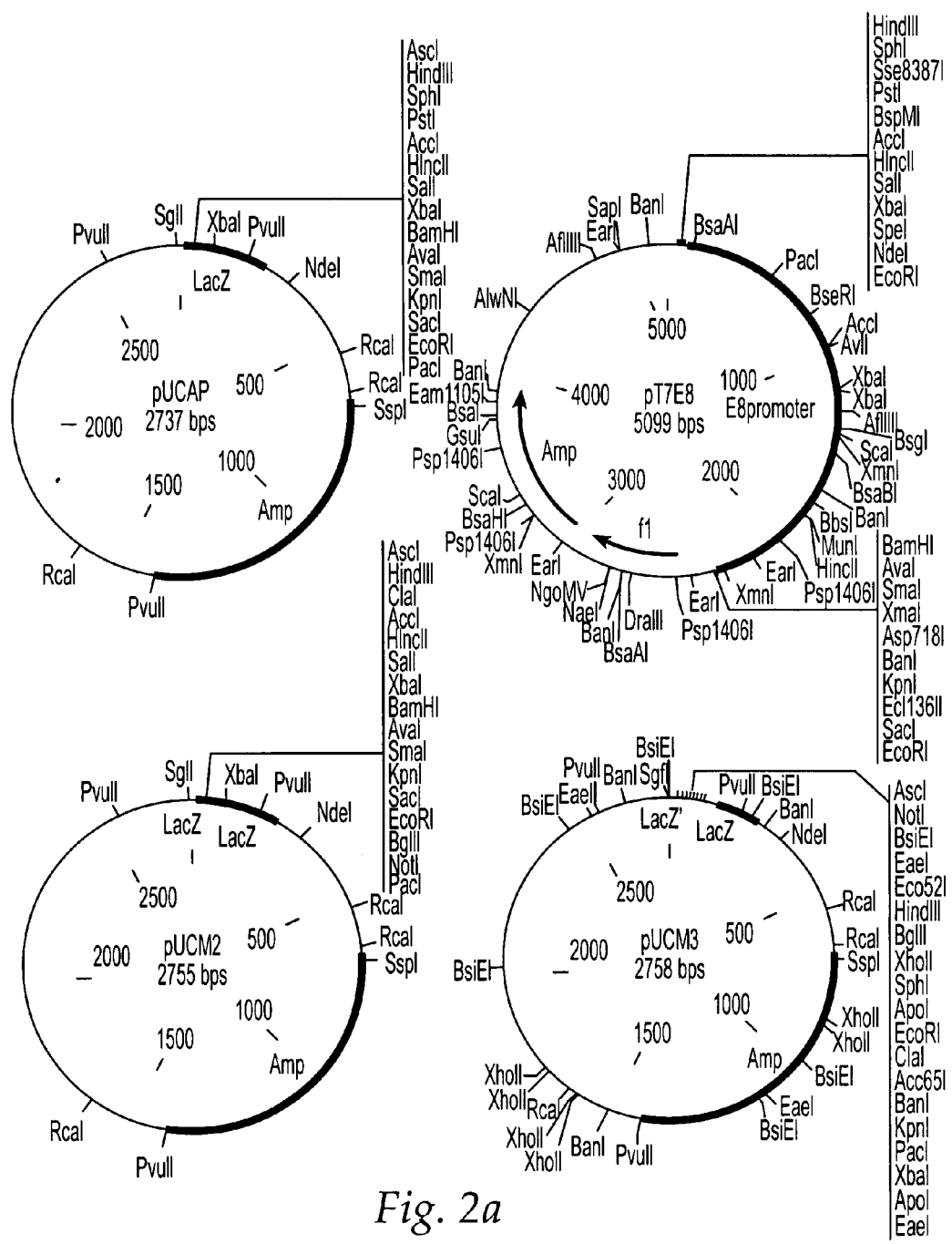

FIG. 2*a*: Plasmid restriction maps of pUCAP, pT7E8, pUCM2 and pUCM3.

Figure 2B:
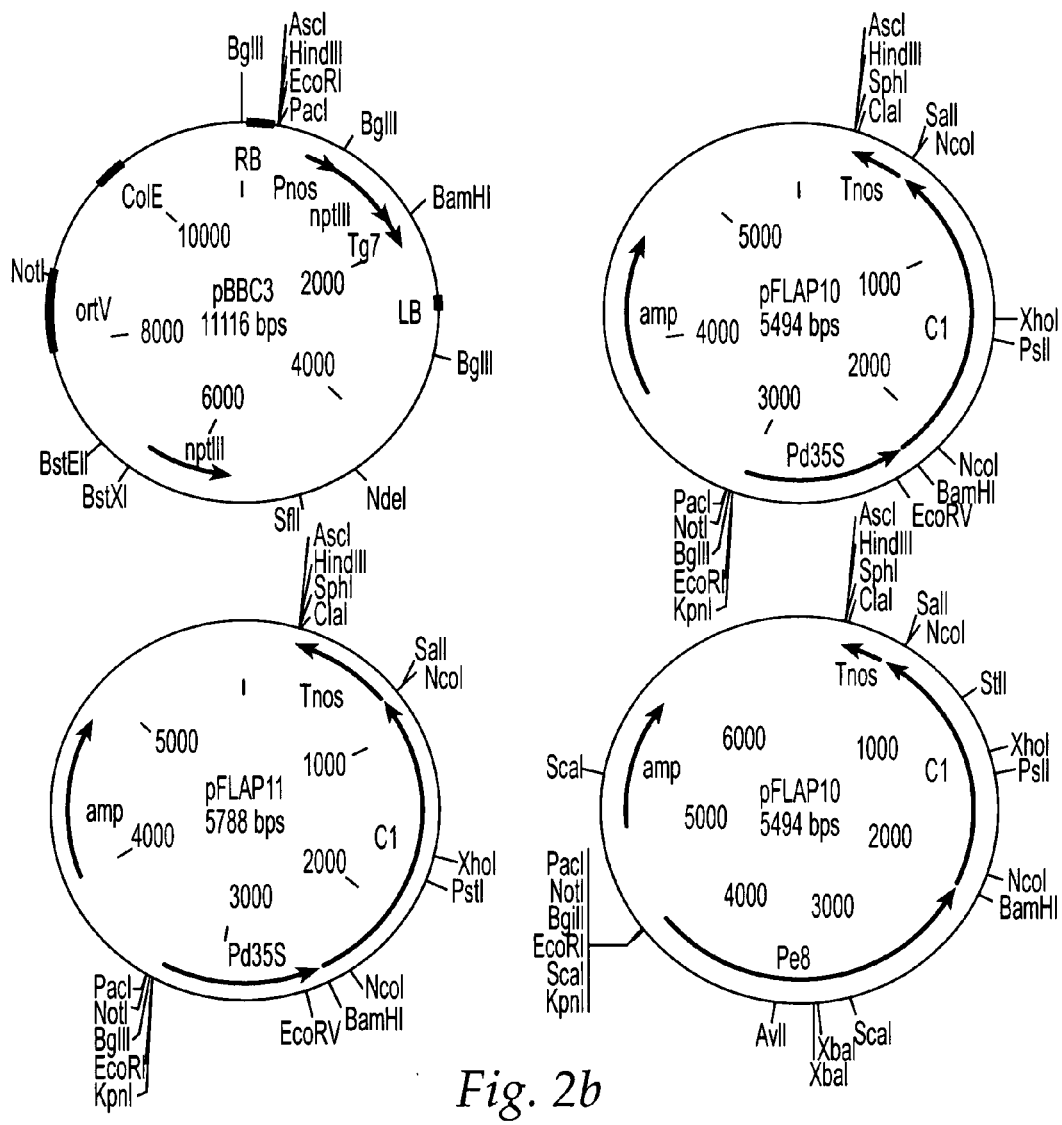

FIG. 2*b*: Plasmid restriction maps of pBBC3, pFLAP10, pFLAP11 and pFLAP15.

Figure 2C:
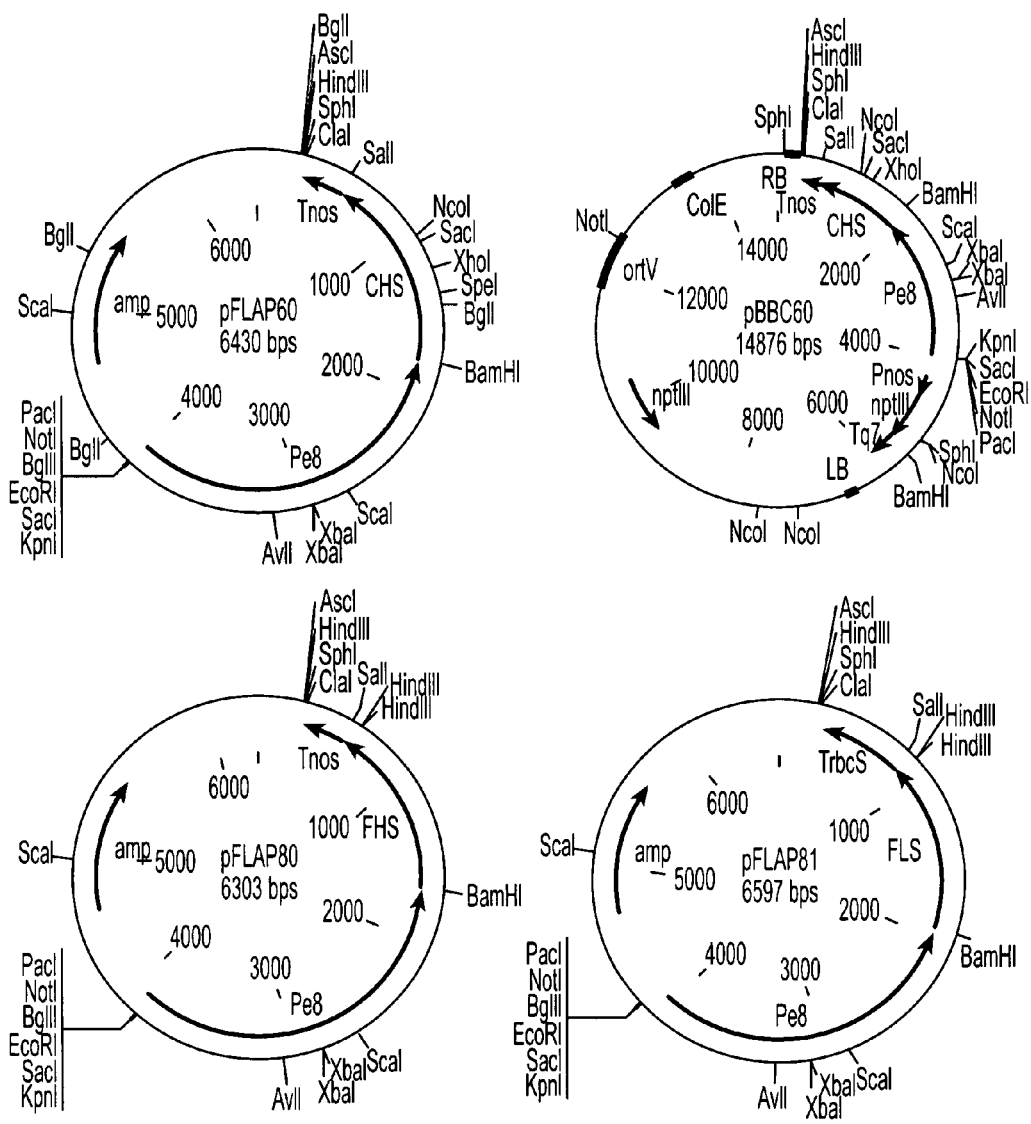

FIG. 2*c*: Plasmid restriction maps of pFLAP60, pBBC60, pFLAP80 and pFLAP81.

Figure 2D:
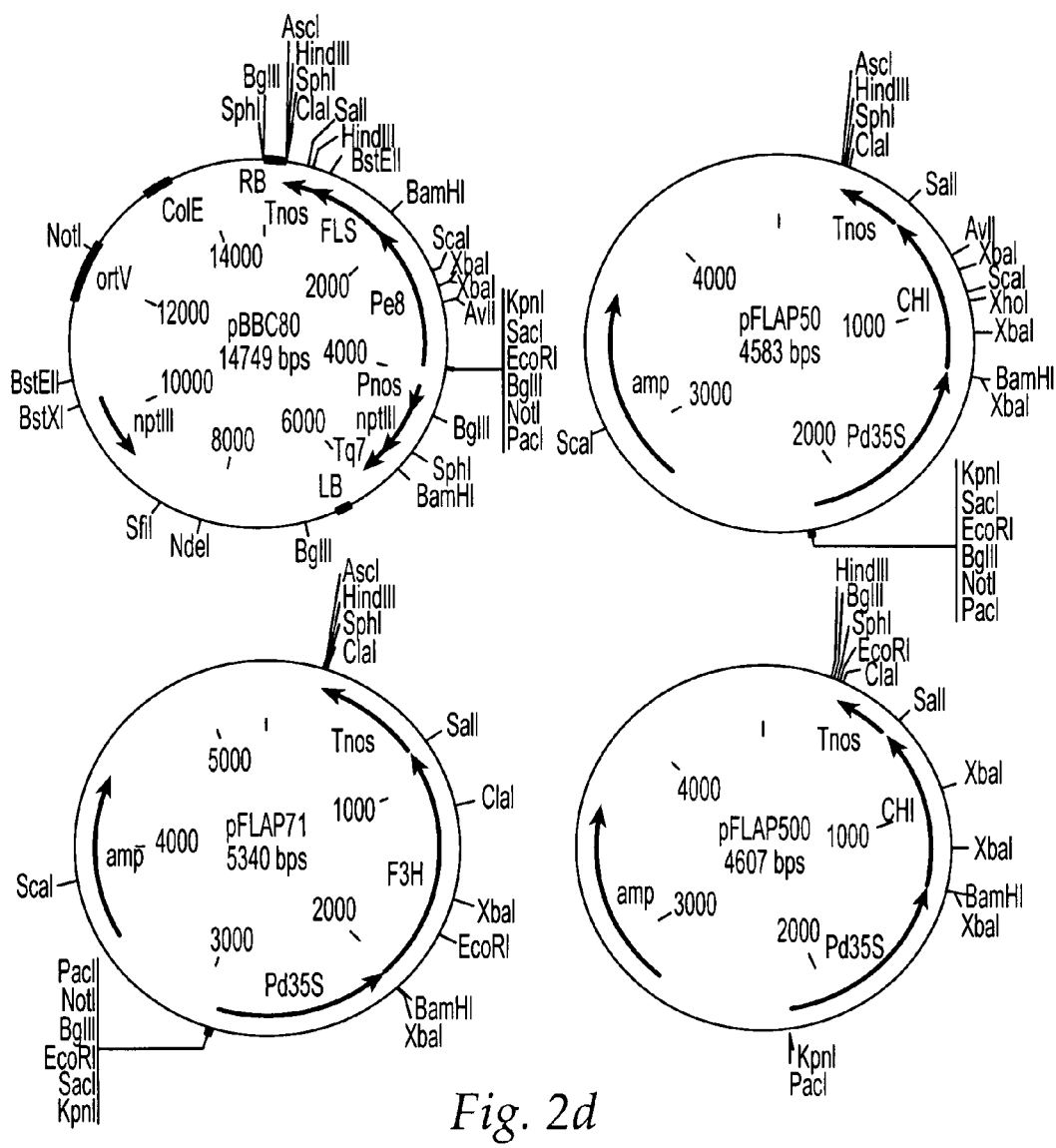

FIG. 2*d*: Plasmid restriction maps of pBBC80, pFLAP50, pFLAP71, and pFLAP500.

Figure 2E:
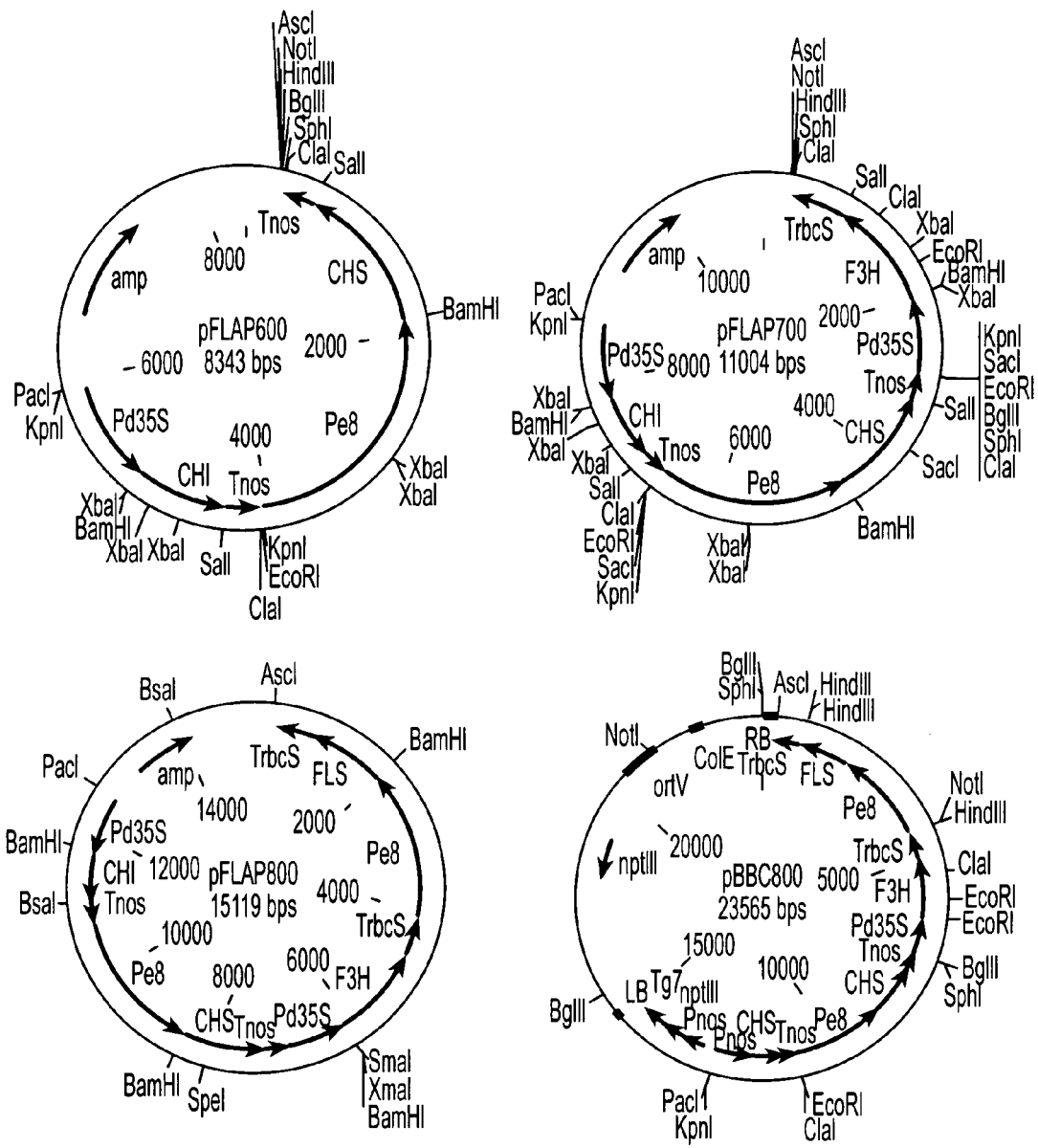

FIG. 2*e*: Plasmid restriction maps of pFLAP600, pFLAP700, pFLAP800 and pBBC800.

Figure 2F:
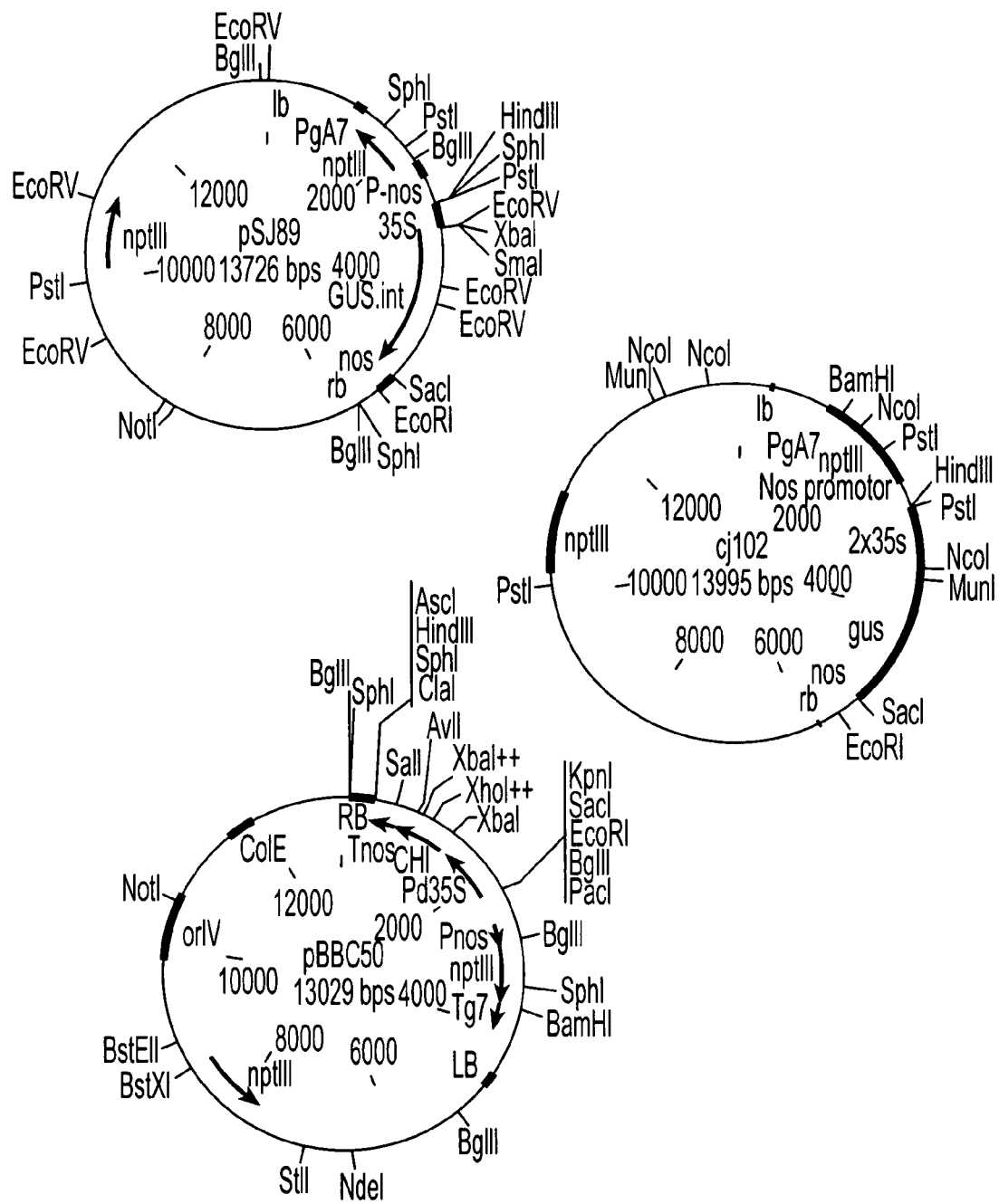
Figure 3A:
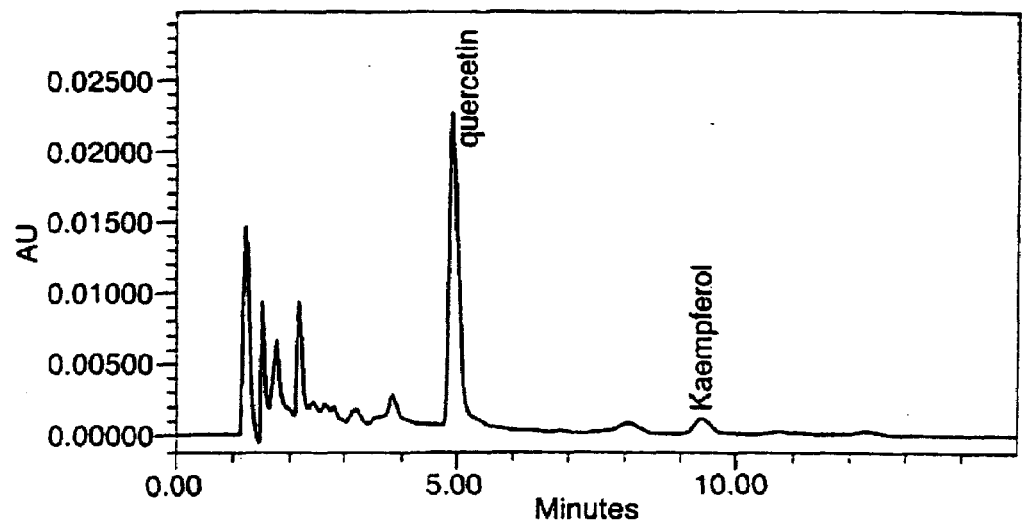
Figure 3A:
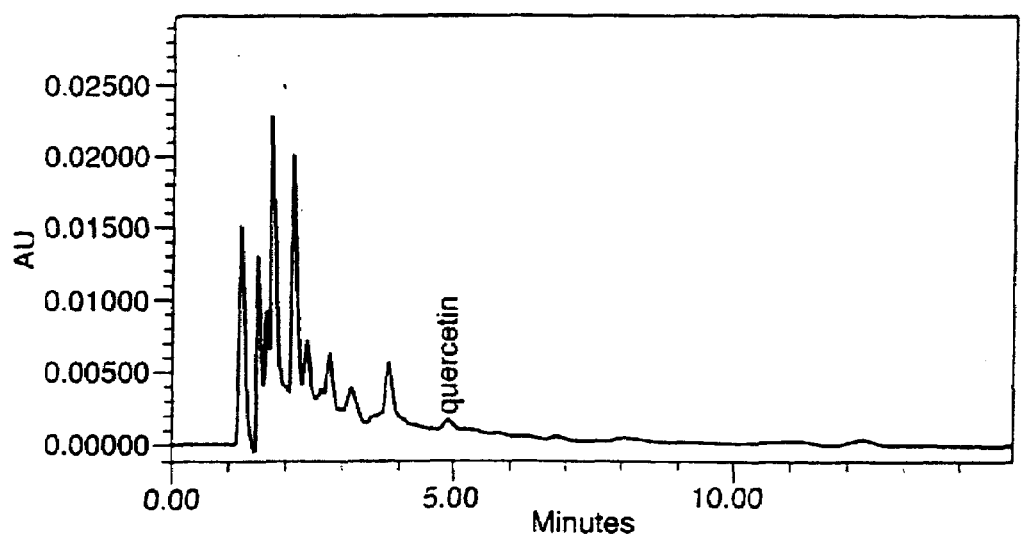
Figure 3B:
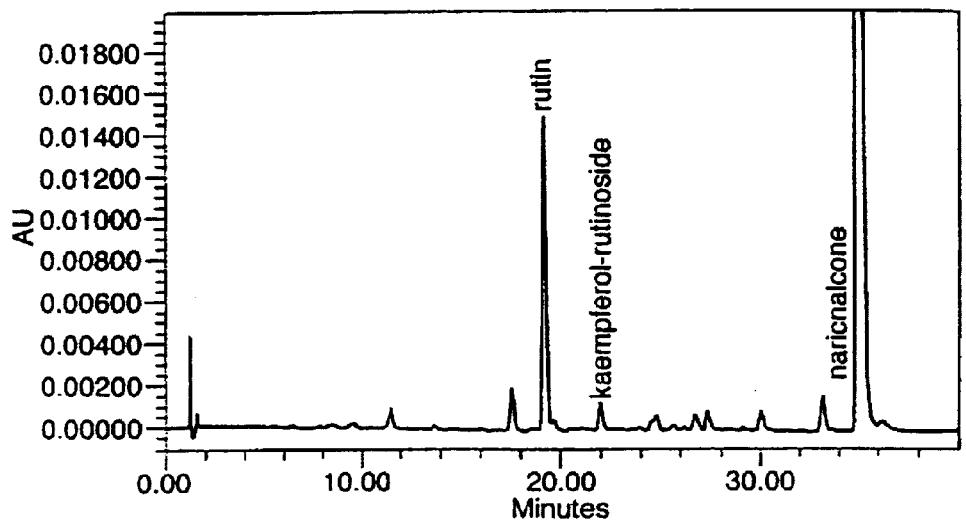
Figure 3B:
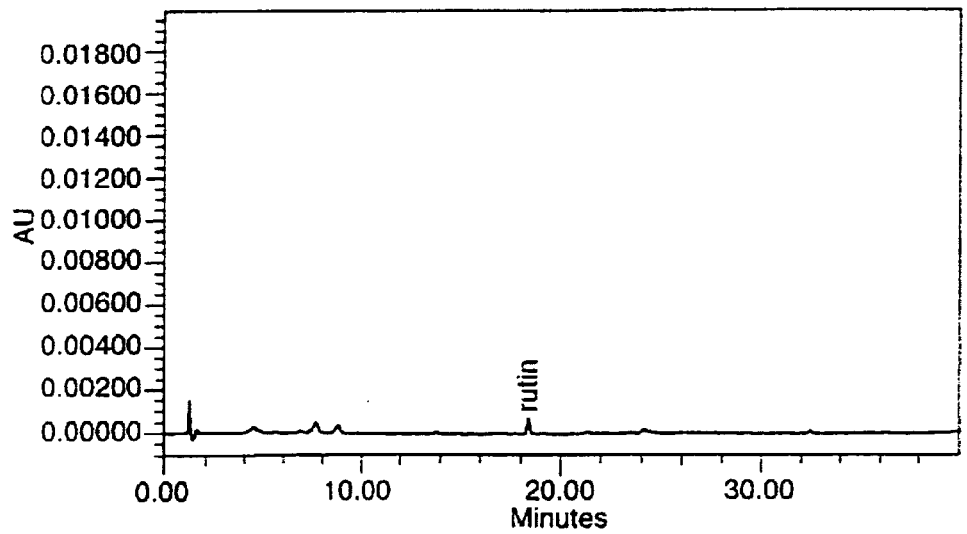

FIG. 2*f*: Plasmid restriction maps of pSJ89, pcJ102 and pBBC50.

FIG. 3: Flavonoid levels from peel and flesh tissues of non-transformed FM6203 tomato fruit in hydrolysed extracts (a) and (b) and non-hydrolysed extracts (c) and (d).

Figure 4:
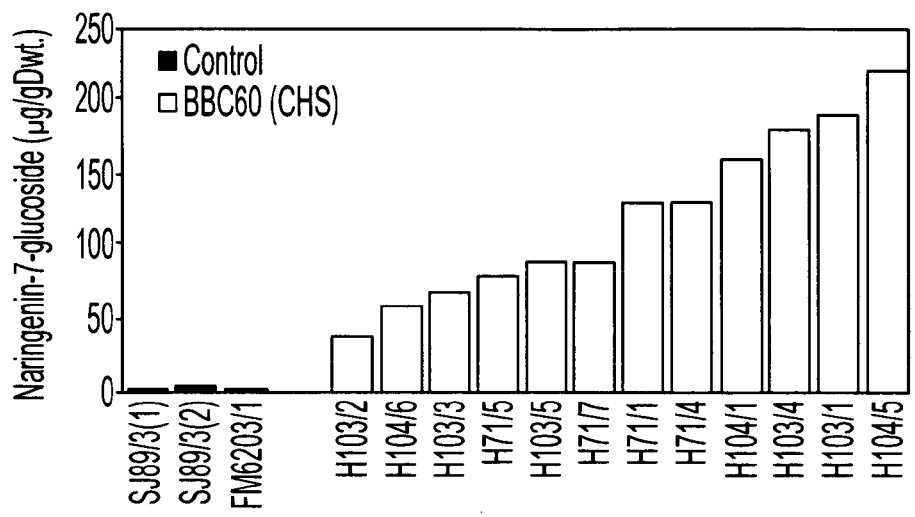
Figure 4:
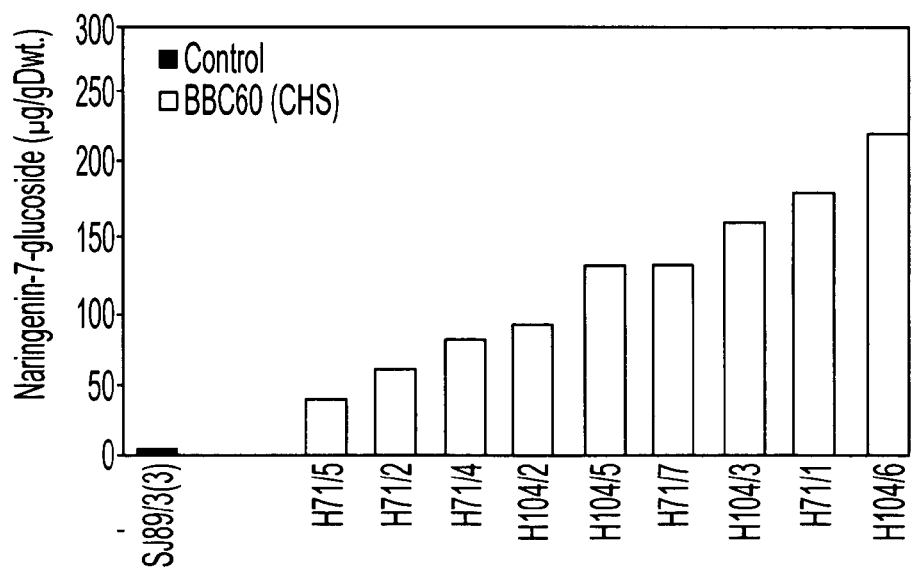

FIG. 4: Level of naringenin-7-glucoside in (A) pericarp and (B) columella tissues from fruit from BBC60 (CHS) and control (pSJ89) transformed tomatoes.

Figure 5:
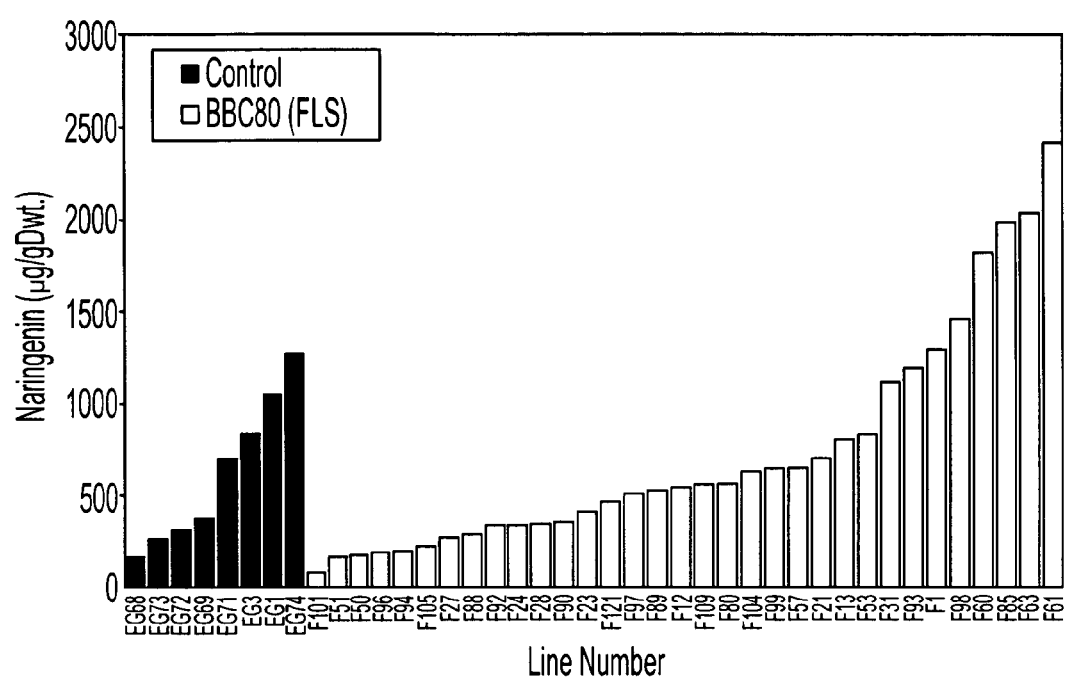

FIG. 5: Naringenin level in hydrolysed peel tissue from $T_o$ fruit from pBBC80 and control (pSJ89) transformed tomatoes.

Figure 6:
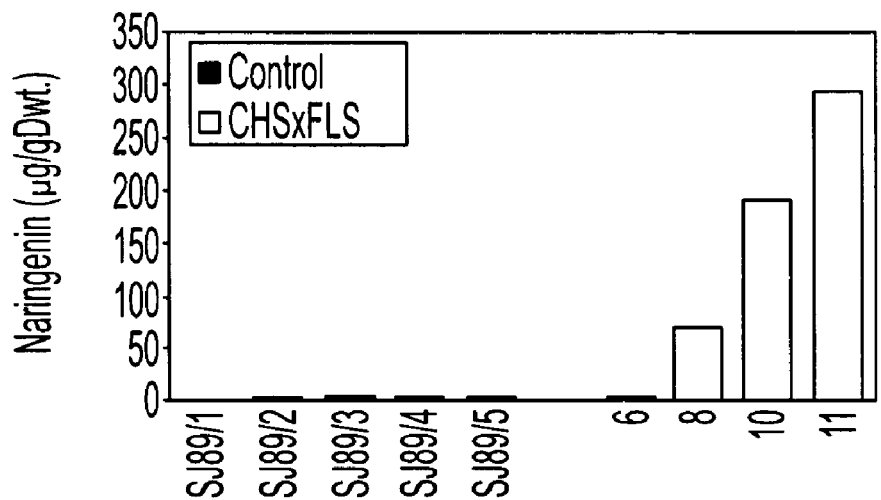
Figure 6:
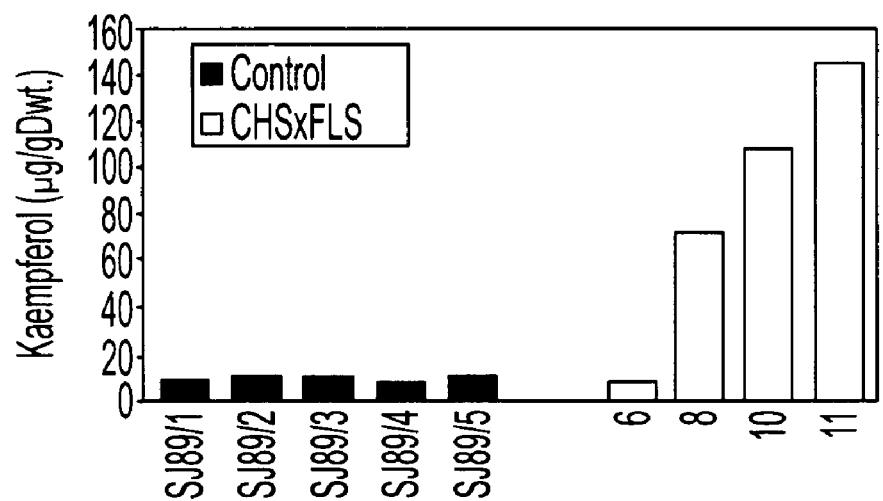

FIG. 6: Naringenin (A) and Kaempferol (B) level in hydrolysed pericarp tissue from CHS×FLS (pBBC60+BBC80) and pSJ89 control fruit.

Figure 7:
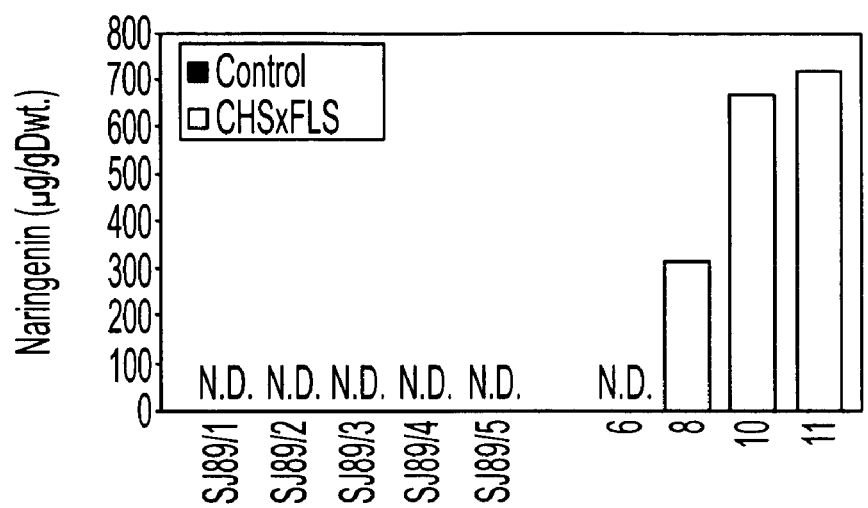
Figure 7:
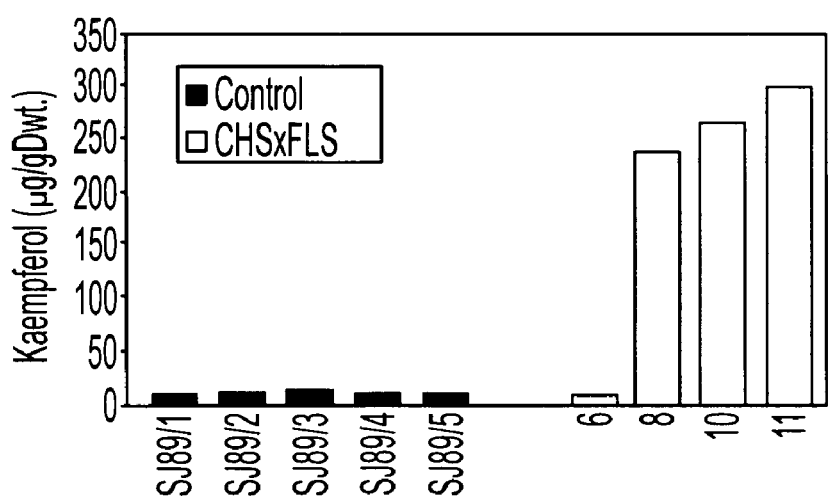

FIG. 7: Naringenin (A) and kaempferol (B) level in hydrolysed columella tissue from CHS×FLS (pBBC60+pBBC80) and control (pSJ89) fruit.

Figure 8:
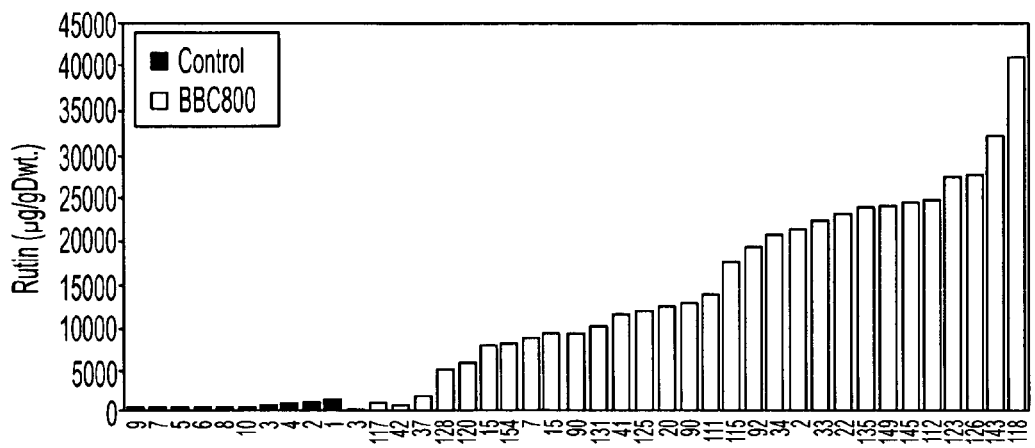
Figure 8:
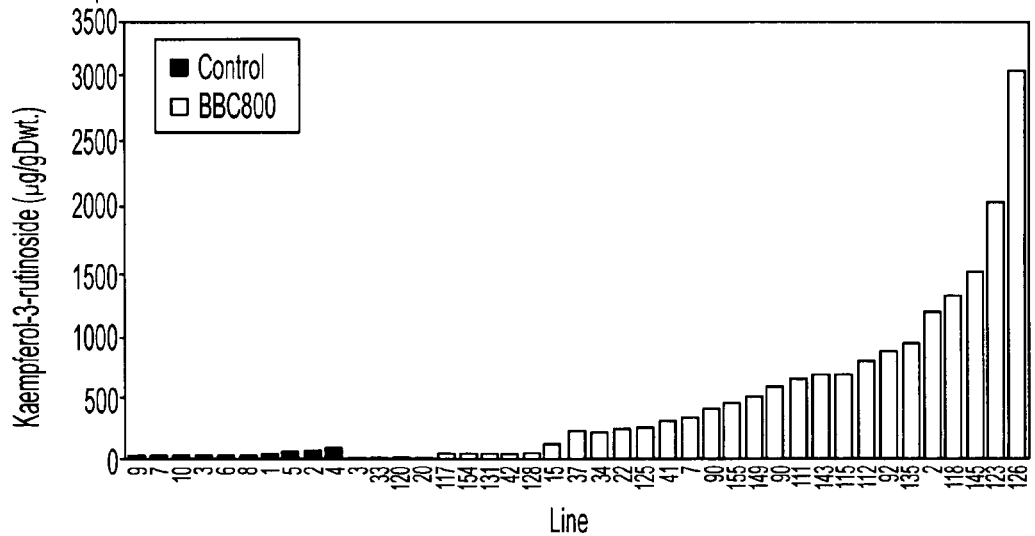

FIG. 8: Level of rutin (A) and kaempferol-3-rutinoslde (B) in non-hydrolysed peel tissue from To fruit from pBBC800 and control (pCJ102) transformed tomatoes.

Figure 9:
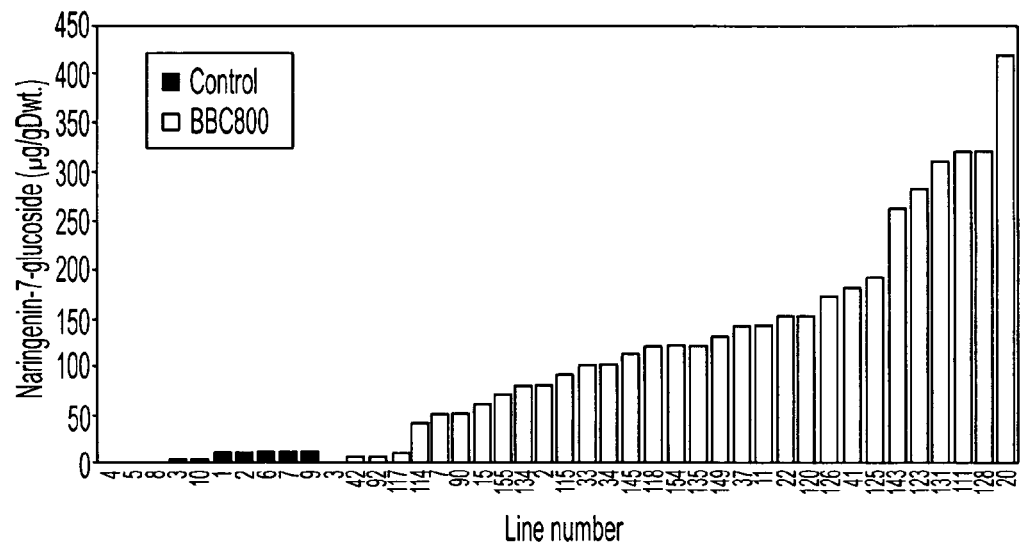

FIG. 9: Accumulation of naringenin-7-glucoside (A) and kaempferol-3-rutinoside-7-0-glucoside (B) in non-hydrolysed columella tissue from To fruit from pBBC800 and control (pCJ102) transformed tomatoes.

FIG. 10: Sequence ID number 1: *Petunia hybrida* (V30) cDNA for chalcone synthase (CHS-a) is obtainable from EMBL database accession number X04080 as published by Koes et al., (1986), Nucleic Acids Res., 14, 5229–5239. Actually cDNA, but referred to as mRNA on the EMBL database.

FIG. 11: Sequence ID number 2: *Petunia hybrida* (V30) amino acid sequence for chalcone synthase (CHS-a) obtainable from SWISS-PROT database, accession number P08894, as published by Koes et al., (1986), Nucleic Acids Res., 14, 5229–5239.

FIG. 12: Sequence ID number 3: *Petunia hybrida* (V30) cDNA sequence for chalcone isomerase (CHI-a) obtainable from EMBL database, accession number X14589, as published by van Tunen et al., (1988), EMBO J., 7, 1257–1263.

FIG. 13 Sequence ID number 4: *Petunia hybrida* (V30) amino acid sequence for chalcone isomerase (CHI-a) obtainable from PIR database, accession number SO4725, as published by van Tunen et al., (1988), EMBO J., 7, 1257–1263.

FIG. 14: Sequence ID number 5: *Petunia hybrida* (V30) cDNA sequence for flavanone-3-hydroxylase (F3H).

FIG. 15: Sequence ID number 6: *Petunia hybrida* (V30) amino acid sequence for flavanone-3-hydroxylase (F3H).

FIG. 16: Sequence ID number 7: *Petunia hybrida* (V30) cDNA sequence for flavonol synthase (FLS).

FIG. 17: Sequence ID number 8: *Petunia hybrida* (V30) amino acid sequence for flavonol synthase (FLS).

EXAMPLES

Example 1

Plant Material

All experiments can be performed using normally available processing tomato lines as the starting material or salad varieties. FM6203 is processing tomato line and is comparable to the commercially available line "Amish paste". Ailsa Craig is a suitable salad variety.

Plants of tomato line FM6203 was grown in a glasshouse with a 16 h photoperiod and a 21/17° C. day/night temperature.

Example 2

Bacterial Strains

The *Escherichia coli* strain used was:
DH5α supE44, D(lacZYA-ArgF)U169, f80lacZDM15, hsdR17 ($r_k-$, $m_k+$), recA1, endA1, gyrA96, thi-1, relA1, deoR (Hanahan, 1983).

The *Agrobacterium* strain used was *Agrobacterium tumefaciens* LBA4404 (Hoekema, 1985).

Transformation of *E. coli* DH5α was performed using the method of Hanahan (1983).

Transformation of *Agrobacterium tumefaciens* LBA4404 was performed according to Gynheung et al., (1988).

Example 3

Analysis of Endogenous Expression of CHS and FLS in Ripening Tomato Fruit

Northern analysis was used to determine the level of expression of the endogenous chs gene(s) and the endogenous fls gene(s), during FM6203 tomato fruit ripening.

Total RNA was isolated from the peel and flesh from FM6203 fruit at green, breaker, turning and red stages of ripening and also from young leaves according to the protocol of Van Tunen et al., (1988). For Northern analysis, 10 μg of total RNA was loaded on formaldehyde agarose gels and separated by electrophoresis at 25V overnight according to Sambrook et al., (1989). Separated RNA was then blotted onto Hybond $N^+$ membrane (Amersham) overnight according to Sambrook et al., (1989).

For detection of endogenous chalcone synthase transcripts, *Petunia hybrida* cDNA fragments encoding chalcone synthase (chs-a) were used as a probe. These fragments were obtained by RT-PCR using total RNA extracted from closed flowers from *Petunia hybrida* W115 as a target with primer combinations F13/F14 (Table 1). The PCR amplification products were verified by sequence analysis prior to hybridisation.

For detection of endogenous flavonol synthase transcripts, Petunia hybrida cDNA fragments encoding flavonol synthase were used as a probe. These fragments were obtained by RT-PCR using total RNA extracted from closed flowers from *Petunia hybrida* W115 as a target with primer combinations F20/F21 (Table 1). The obtained PCR products were verified by sequence analysis prior to hybridisation.

CHS and FLS probes were radio-labelled with $^{32}P$ and purified according to methods given in Gibco Life Technologies RadPrime Labelling system. Blots were hybridised overnight at 55° C. and washed three times in 2×SSC, 0.1% SDS, 55° C., 30 min, before being exposed to X-ray film for 48 hr.

The autoradiographs from the northern blot analysis are shown in FIG. 1. Both the chs and fls transcripts are abundantly present in the peel tissue of tomato fruit from all developmental stages tested. Accumulation of both the chs and fls transcripts peak during the 'breaker' and 'turning' stages of development and subsequently decrease in the 'red' stage.

In the flesh of tomato fruit, the levels of both chs and fls transcripts were very low at all stages of fruit development. This finding is in agreement with HPLC data that showed only trace amounts of naringenin and flavonol compounds in this tissue (Example 7). It is noteworthy that both Chs and fls transcripts are present in low but a detectable level in tomato leaves.

Example 4

Gene Constructs

4.1 Strategy to Coordinately Express Flavonoid Biosynthesis Genes in Tomato Fruits During the ripening of tomato fruit the expression levels of the chs and fls genes are abundant in the peel but remain low in the flesh.

The production of flavonoids in tomato fruits is increased by coordinate expression of the *Petunia hybrida* flavonoid biosynthetic enzymes chalcone synthase and flavonol synthase. To increase the level of flavonoids predominantly in the fruit of tomato the chalcone synthase and flavonol synthase genes are expressed under the control of the fruit specific tomato E8 promoter.

4.2 Gene Constructs

The different components of the gene fusions and the different plasmid vectors constructed were obtained as follows. Plasmid vector PUCAP (Van Engelen et al., 1995) was provided by CPRO-DLO. Binary vector pGPTV-KAN (Becker et al., 1992) was provided by Unilever. The nos terminator (Tnos) was amplified from plasmid pBI121 (Jefferson et al., 1987). Plasmid vector pAL77, used for construction of pFLAP10, was obtained from R. W. Davies (Stanford University, Lloyd et al., 1992). The double enhanced CaMV 35s promoter (Pd35s) was isolated from plasmid pMOG18 (Symons et al., 1990). The tomato E8 promoter (PE8) was PCR amplified from tomato genomic DNA (variety Moneymaker) using Taq polymerase and primers E851 and E8A2 (Table 1). E851 and E8A2 hybridise to the distal (5') and proximal (3') ends of the E8 promoter respectively. The resulting 2.2 kb PCR fragment was then ligated into the EcoRV site of pT7 Blue-T vector (available from Novagen). This resulted in a vector with the E8 promoter inserted in clockwise orientation (same as lac Z gene), which was called pT7E8 (FIG. 2a). All components were cloned as described below.

4.2.1 Construction of Plasmids pUCM2 and pUCM3

To construct plasmid pUCM2, the multiple-cloning-site of plasmid pUCAP (FIG. 2a) was modified by the insertion of two adapters. First, adapter F1/F2 (Table 1), containing the restriction sites SalI/ClaI/SphI, was ligated with plasmid pUCAP restricted with SalI/SphI. This resulted in plasmid pUCM1. Next, adapter F3/F4 (Table 1), consisting of PacI/NotI/BglII/EcoRI restriction sites was ligated into plasmid pUCM1 restricted with PacI/EcoRI. This resulted in plasmid pUCM2 (FIG. 2a). To construct plasmid pUCM3, plasmid pUCAP was digested with PacI/AscI and the whole multiple-cloning-site was replaced by adapter F5/F6 (Table 1). This resulted in plasmid pUCM3 (FIG. 2a).

4.2.2 Construction of pBBC3.

To construct plasmid pBBC3, adapter F38/F39 (Table 1) was ligated into plasmid pGPTV-KAN digested with EcoRI/HindIII. This replaced the gusA-Tnos gene in pGPTV-KAN with a small multiple cloning site consisting of PacI/EcoRI/HindIII/AscI restriction sites (FIG. 2b).

4.2.3 Construction of pFLAP10

Firstly, Tnos was amplified by PCR from pBI121 using primers F12 and AB13 (Table 1). The resulting 250 bp amplification product was ligated into pUCM2 as a SalI/ClaI fragment.

Secondly, the C1 gene was cloned as a BamHI/SalI fragment upstream of Tnos as follows. The C1 gene was firstly transferred as an ~2 kb EcoRI fragment from plasmid pAL77 to the high-copy number plasmid pBluescript SK-, resulting in plasmid pBLC1. The C1 gene was then isolated from pBLC1 as a 1.6 kb EcoRI/PacI fragment and adapters F7/F8 and F9/F10(Table 1) were ligated to each end of the fragment. Ligation of adapters F7/F8 and F9/F10 add unique BamHI and SalI restriction sites to both ends of the gene and remove the existing EcoRI and PacI sites. The resulting fragment was restricted with BamHI/SalI and the C1 fragment ligated upstream of the nos terminator, resulting in plasmid pFLAP2.

Thirdly, Pd35s was cloned as a KpnI/BaI fragment upstream of C1 in pFLAP2 as follows. To create a unique BamHI site at the 3' end of the d35s promoter, plasmid pMOG18 was digested with EcoRV/BamHI thus removing the 3' part of the d35s promoter and the gusA gene. The 3' part of the 35s promoter present in plasmid pAB80 (Bovy et al., (1995)) was then ligated as a 0.2 kb EcoRV/BamHI fragment into the pMOG18 vector, resulting in plasmid pMOG18B. To create a unique KpnI site at the 5' end of the d35s promoter plasmid pMOG18B was then digested with EcoRI, the ends were polished with Klenow polymerase, and subsequently digested with BamHI. The resulting 0.85 kb blunt/BamHI d35s promoter fragment was cloned into plasmid pBLC1 digested with XhoI/polished with Klenow polymerase/BamHI. This resulted in plasmid pBld35S. Finally, the d35s promoter was transferred as a KpnI/BamHI fragment from pBld35s to plasmid pFLAP2. This resulted in plasmid pFLAP10 (FIG. 2b).

4.2.4 Construction of pFLAP11.

pFLAP11 was constructed by replacing the nos terminator of pFLAP10 with the rbcS terminator sequence by cloning downstream of the C1 gene as follows. The rbcS terminator was present as a ~664 bp fragment on plasmid pFLA220. The rbcS terminator was amplified from plasmid pFLAP20 using primer combination F75/M13 rev (Table 1). The primer F75 contains a unique Sal1 site introducing a Sal1 site at the 5' end of the rbcS terminator. The ~664 bp amplification product was restricted with Sal1 and Cla1 and ligated with pFLAP10 which had been restricted with the same enzymes. This resulted in plasmid pFLAP11 (FIG. 2b).

4.2.5 Construction of pFLAP15 pFLAP15 was constructed by replacing the Pd35s promoter of pFLAP10 with the tomato E8 promoter by cloning upstream of the C1 gene as follows. The E8 promoter was present as a 2.2 kb fragment on plasmid pT7E8. This E8 promoter fragment contained an unwanted PacI site at position 430 relative to the 5' end. To remove this PacI site, plasmid pT7E8 was digested with PacI, the ends were polished with T4 DNA polymerase, and the plasmid was self-ligated, resulting in plasmid pT7E8-Pac. The E8 promoter was subsequently amplified from this plasmid by PCR with primers F23 and F26 (Table 1), which contained unique KpnI and BamHI restriction sites respectively. The PCR product was digested with these enzymes and cloned upstream of the C1 gene in plasmid pFLAP10. This resulted in plasmid pFLAP15 (FIG. 2b).

4.3 *Petunia hybrida* chs-a Cloning

4.3.1 Cloning of the chs-a cDNA from *Petunia hybrida*

The chs-a cDNA was amplified from plasmid pFBP176, with primer combination F13/F14 (Table 1). pFBP176 contains the complete 1.2 kb *Petunia hybrida* chs-a cDNA (Koes et al., 1988) cloned as an EcoR1-HindIII fragment into pEMBL18 (available from Boehringer Mannheim; Dente and Cortese, 1987). The primers F13 and F14 contain a 5' extension with a unique BamH1 (F14) and SalI(F13) restriction site. This results in a 1.2 kb chs-a fragment.

4.3.2 Construction of the chs-a Gene Fusion

The PE8-chs-a-Tnos gene construct was made as follows:

The chs-a gene was amplified from the plasmid pFBP176, using primers F14 and F13 which added either BamH1 or SalI restriction sites respectively. The 1.2 kb PCR amplification product was restricted with these enzymes and ligated downstream of the E8 promoter into pFLAP15 restricted with the same enzymes. This resulted in plasmid pFLAP60 (FIG. 2c).

4.3.3 Construction of pBBC60

The PE8-chs-a-Tnos insert of plasmid pFLAP60, containing the chs-a gene, was transferred as a PacI/AscI fragment to binary vector pBBC3. The resulting plasmid, pBBC60 (FIG. 2c) was used for transformation of FM6203.

4.4 *Petunia hybrida* fls Cloning 4.4.1 Cloning of the fls Gene from *Petunia hybrida*

The fls gene was amplified from a *Petunia hybrida* petal cDNA library using primers, F20 and F21 (Table 1). These primers contain a 5' extension with a unique BamH1 (F20) and SalI(F21) restriction site. This results in a 1.14 kb fls fragment.

4.4.2 Construction of the fls Gene Fusion

The PE8-fls-Tnos gene construct was made as follows:

Firstly, the FLS gene was amplified from a Petunia petal cDNA library using primers F20 and F21. The 1.14 kb PCR product was restricted using BamH1 and SalI and ligated downstream of the E8 promoter into plasmid pFLAP15 or pFLAP11 restricted with the same enzymes. This resulted in plasmids pFLAP80 and pFLAP81 respectively (FIG. 2c).

4.4.3 Construction of pBBC80

The PE8-fls-Tnos insert from plasmid pFLAP80, containing the fls gene, was transferred as a PacI/AscI fragment to binary vector pBBC3. The resulting plasmid, pBBC80 (FIG. 2d) was used for transformation of FM6203.

4.5 *Petunia hybrida* chi-a Cloning 4.5.1 Cloning of the chi-a Gene from *Petunia hybrida*

The chi-a gene was amplified from plasmid pMIP41 (kindly supplied by Dr. A. vanTunen), with primer combination F15/F16 (Table 1). pMIP41 contains the complete chi-a cDNA from *Petunia hybrida* inbred line V30. The primers F15 and F16 contain a 5' extension with a unique BamHI(F15) and SalI (F16) restriction site. This results in an ~0.75 kb chi-a fragment.

4.5.2 Construction of the chi-a Gene Fusion

The d35S-chi-a-Tnos gene construct was made as follows:

The chi-a gene was amplified from the plasmid pMIP41, using primers F15 and F16 which added either BamH1 or SalI restriction sites respectively. The ~0.75 kb amplification product was restriction with these enzymes and ligated downstream of the d35S promoter into pFLAP10 restricted with the same enzymes. This resulted in plasmid pFLAP50 (FIG. 2d).

4.6 *Petunia hybrida* f3h Cloning 4.6.1 Cloning of the f3h Gene from *Petunia hybrida*

A 500 bp f3h fragment was amplified from a *Petunia hybrida* petal cDNA library using primers, F48 and F51 (Table 1). This fragment was used to isolate a full-length f3h cDNA by plaque hybridisation. Nine positive plaques were purified and the pBluescript plasmids containing cDNA inserts were excised from the phages by in vitro excision and sequenced. One clone contained a complete F3H open reading frame and was designated pF3Hc.

4.6.2 Construction of the f3h Gene Fusion

The d35S-f3h-Tnos gene construct was made as follows. The F3H cDNA was restricted from pF3Hc as a BamH1-XhoI fragment and ligated with pFLAP11 restricted with the same enzymes. This resulted in plasmid pFLAP71 (FIG. 2d).

4.7 Construction of pBBC800 (PE8-chs-a-Tnos-P35S-chi-a-Tnos-Pd35S-f3h-Trbcs-PE8-fls-Trbcs)

The single-gene constructs described above were used to construct plasmid pBBC800 as follows:

The inserts of plasmids pFLAP50, pFLAP60, pFLAP71 and pFLAP81 were cloned behind each other in plasmid pUCM3 to make the plasmid pFLAP800.

Firstly, the pFLAP50 was digested with KpnI/ClaI and the chi insert was cloned in plasmid pUCM3 cut with the same enzymes. This resulted in plasmid pFLAP500 (FIG. 2d). Secondly, the chs insert of plasmid pFLAP60 was ligated as a EcoRI/SphI fragment behind the chi gene in plasmid pFLAP500, resulting in plasmid pFLAP600 (FIG. 2e). Thirdly, the f3h gene of plasmid pFLAP71 was ligated as a BgIII/HinDIII fragment behind the chs gene in pFLAP600, resulting in plasmid pFLAP700 (FIG. 2e). Fourthly, the fls insert of plasmid pFLAP81 was ligated as a NotI/AscI fragment behind the f3h gene in plasmid pFLAP700, resulting in plasmid pFLAP800 (FIG. 2e). Finally, the 12 kb insert of plasmid pFLAP800, containing the four structural genes, was transferred as a PacI/AscI fragment to binary vector pBBC3. The resulting plasmid, pBBC800 (FIG. 2e) was used for transformation of FM6203.

4.8 GPTV Control Plasmid

A GPTV-based binary plasmid containing the β-glucuronidase gene (with the st-ls1 intron; Vancanneyt et al. 1990) was used as a control plasmid to transform FM6203). This allows direct comparison between gus transformed control plants and plants containing the chs-a and fls constructs generated via a tissue culture procedure.

4.8.1 pSJ89

A GPTV-based binary plasmid containing the β-glucuronidase gene (with the st-ls1 intron; Vancanneyt et al. 1990) under control of the CAMV 35s promoter and the nos poly(A) signal (P35s-gusA-Trnos).

Plasmid pSJ89 was constructed as follows: the CAMV 35s promoter-gus-int fragment from plasmid p35SGUSINT (Vancanneyt et al. 1990) was ligated as a HindIII-SacI fragment into the plasmid pSJ34 restricted with the same enzymes. This resulted in plasmid pSJ89 (FIG. 2f). pSJ34 is a derivative of the binary vector pGPTV-KAN (Becker et al. 1992) in which the BamHI site between the NPTII selectable marker and the gene 7 poly(A) signal was destroyed by 'filling-in' with klenow polymerase.

4.8.2 pCJ102

A GPTV-based binary plasmid containing the β-glucuronidase gene (with the st-ls1 intron; Vancanneyt et al. 1990) under control of the double CaMV 35s promoter and the nos poly(A) signal (Pd35s-gusA-Tnos).

Plasmid pCJ102 was constructed as follows: oligonucleotide primers 167 and 168 (Table 1) were used to amplify the 460 bp 5' fragment of the GUS gene (from vector pSJ34) and modifying the 5' end to create a NcoI site and thus modifying the second amino acid. The PCR amplified fragment was digested with NcoI and EcoRV and ligated with the HindIII/EcoRI vector fragment of pSJ34 together with the HindIII/

NcoI 2x35S promoter fragment of pPV5LN and the EcoRV/EcoRI 3' GUS-Nos terminator fragment of pSJ34, yielding the vector pCJ102 (FIG. 2f).

Example 5

Stable Transformation of Tomato Line FM6203.

5.1 *A. tumefaciens* Transformation

Binary plasmids of pBBC60, pBBC80 and pSJ89 were introduced into *Agrobacterium tumefaciens* strain LBA4404 by adding 1μg of plasmid DNA to 100 μl of *A. tumefaciens* cells competent of DNA uptake. Competent cells of *A. tumefaciens* were prepared by inoculation of 50 ml of YEP medium (Sambrook et al., 1989) and culturing with shaking at 100 rpm at 28° C. until the culture reached an $OD_{600}$ of 0.5–1.0. The cells were then harvested by centrifugation and the supernatant discarded before re-suspension in 1 ml of 50 mM $CaCl_2$ solution and dispensing into 100 μl aliquots.

The DNA-*Agrobacterium* mixture was flash-frozen in liquid nitrogen before thawing rapidly by placing in a water bath at 37° C. After the addition of 1 ml YEP medium the bacteria were incubated at 28° C. for 4 hours with gentle shaking. Finally, transformed bacteria were selected on YEP-agar plates supplemented with 50 μg/ml kanamycin. The presence of the plasmids in kanamycin resistant clones was tested by PCR analysis using pBBC60 (CHS S1 and NosAs), pBBC80 (FLSs1 and FLSas1) or pSJ89 (30035S and Gus2) specific primers respectively (Table 1).

5.2 Tomato Transformations

Seeds from tomato line FM6203 were surface sterilised by incubation in 1.5% hypochlorite for 2 hours before washing seeds well with three rinses of sterile water. The surface sterilised seeds were then germinated and the seedlings grown for 8 days on a 1:1 mixture of vermiculite and MS medium (Murashige and Skoog, 1962; Duchefa) supplemented with 0.3% (w/v) sucrose, with a photoperiod of 16 h (3000 lux) at 25°C.

For transformation, eight-day old cotyledons were cut into 25 $mm^2$ squares and 'pre-incubated' for 24 h on tobacco suspension feeder-layer plates at low light intensity (1000 lux). The tobacco leaf suspension culture was maintained in MS salts supplemented with Gamborgs B5 vitamins, sucrose (3% w/v), 2,4-dichlorophenoxyacetic acid (2,4-D; 1.0 mg/l) and benzylaminopurine (BAP; 0.2 mg/l). Tobacco suspension feeder-layer plates were prepared by transferring 2 ml of cell suspension culture to the surface of solidified MS media (MS salts supplemented with Gamborgs B5 vitamins, sucrose (3% w/v), agarose (6 g/l), 2,4-dichlorophenoxyacetic acid (2,4-D; 1.0 mg/l), benzylaminopurine (BAP; 0.2 mg/l) and 100 mg/l inositol) and overlaying the cells with sterile filter paper.

A single colony from the Agrobacterium LBA4404 cultures containing one of the binary vectors mentioned in Example 4 was grown for 48 h in liquid Minimal A medium (Sambrook et al., 1989) supplemented with 50 μg/ml kanamycin to an $OD_{600}$ of 0.5–1.0. The bacteria were pelleted by centrifugation and resuspended in MS medium supplemented with Gamborgs B5 vitamins (Duchefa) and 3% (w/v) sucrose at an $OD_{600}$ of 0.5. The cotyledon explants were then incubated in the *A. tumefaciens* suspension for 30 min, blotted dry on filter paper and co-cultivated for 48 h on tobacco feeder layer plates at 25° C. and low light intensity.

After co-cultivation, the explants were transferred to regeneration medium, consisting of MS medium supplemented with Nitsch vitamins, sucrose (2% w/v), agargel (5 g/l), zeatin-riboside (2 mg/l), kanamycin (100 mg/l) and cefotaxime (500 mg/l). Regenerating explants were transferred to fresh medium every two weeks. Kanamycin resistant shoots were transferred to rooting medium, consisting of MS medium supplemented with Gamborgs B5 vitamins, sucrose (0.5% w/v), gelrite (2 g/l), kanamycin (50 mg/l) and cefotaxime (250 mg/l). During regeneration and rooting, transformed plantlets were maintained in a growth chamber at 25° C. with a 16 h photoperiod (3000 lux). After root formation, plantlets were transferred to soil and grown in the glasshouse.

Transgenic plants harbouring the constructs pBBC60, pBBC80, pBBC800 and pSJ89 were selected following specific amplification of the chs-a, fls, chi, f3h or gus transgenes respectively.

Example 6

Measurement of Flavonoids in Tomato Fruits 6.1 Growth and Harvest of Tomato Fruits Tomato plants were grown in 10 liter pots in a greenhouse under standard growth conditions (day/night temperatures 22° C./17° C., 16 h light). Fruits were harvested at fully red, ripe stage (18–21 dpa). For discrimination between flavonoids in peel and in flesh tissue, the outer layer of about 1 mm thick (i.e. cuticula, epidermal layer plus some sub-epidermal tissue) was separated from the fruit using a scalpel and classified as peel. The columella was excised from the remaining flesh tissue and seeds and jelly-like parenchyma removed, this tissue was classified as columella. The remainder of the fruit flesh tissue was classified as pericarp. After separation, tissues were frozen in liquid nitrogen, ground to a fine powder and stored at −80° C. until use.

6.2 Extraction of Flavonoids from Tomato Tissues

Flavonoids were determined as their glycosides or as aglycones by preparing non-hydrolysed and hydrolysed extracts, respectively.

Preparation of hydrolysed extracts was based on the method described by Hertog et al., (1992). Frozen tissues were ground to a fine powder, using a coffee grinder, before tissues were lyophilized for 48 h. For flavonoid extraction, fifty mg of freeze-dried material was transferred to a 4 ml reacti-vial. To each sample, 1.6 ml of 62.5% methanol (HPLC grade) in distilled water and 0.4ml of 6M HCl was added. The vials were sealed, using screw caps containing a teflon inlay, before incubating for 60 min at 90° C. in a waterbath. After incubation (hydrolysis), the tubes were cooled on ice, before the addition of 2 ml of 100% methanol and sonicated for 5 min.

For determination of flavonoid-glycosides and naringenin-chalcone, 50 mg of lyophilized tomato tissue was added to 4 ml of 70% aqueous methanol in a reacti-vial. The vials were closed with screw caps containing a teflon inlay. Extraction was carried out by ultrasonicating for 30 min at room temperature (~25° C.) with occasional additional mixing.

Using flavonoid standards (obtained from Apin Chemicals Ltd, Abingdon, UK) it was established that complete hydrolysis of the flavonoid glycosides was achieved, whilst ~95% of naringenin-chalcone was chemically converted into naringenin. Furthermore, the recovery of quercetin, kaempferol and naringenin standards following addition to peel or flesh extracts immediately prior to hydrolysis was greater than 90%.

6.3 HPLC Conditions for Flavonoid Analysis

After sonication, a 1 ml aliquot from each extract was filtered through a 0.2 μm PTFE disposable filter (Whatman) and 20 μl from the filtrate was injected into the HPLC system.

The solvent delivery system was an HP1100 (Hewlett Packard), incorporating a cooled HP1100 autosampler maintained at 4° C. with a fixed 20 μl loop, and a Prodigy $C_{18}$ (4.6×150 mm, particle size 5 μm) analytical column (Phenomenex). The column was placed in a HP1100 column oven set at 30° C. A photodiode array detector (HP1100) was used to record the spectra of compounds eluting from the column on-line. The detector was set to record absorbance spectra from 200 to 550 nm with a resolution of 2 nm, at a time interval of 2 seconds.

Chemstations software (Hewlett Packard, version 6.) was used to control the solvent delivery system and the photodiode array detector.

HPLC separation of flavonoids in non-hydrolysed extracts (flavonoid-glycosides and naringenin-chalcone) was performed using a gradient of acetonitrile in 0.1% TFA, at a flow rate of 1.0 ml/min: 10–17.5% linear in 8 min, then 17.5–25% in 12 min, a hold at 25% for 22 min followed by a 4 min washing with 50% acetonitrile in 0.1% TFA. After washing, the eluent composition was brought to the initial condition for 5 min, before next injection. HPLC separation of flavonoids present in hydrolysed extracts (flavonol aglycones and naringenin) was carried out under isocratic conditions of 25% acetonitrile (HPLC) in 0.1% trifluoroacetic acid (TFA) at a flow rate of 0.9 ml/min.

Table 2 summarizes the retention times, obtained with the two different HPLC separation methods, of some flavonoid standards.

HPLC data were analyzed using Chemstations software (Hewlett-Packard version 6.). Absorbance spectra (corrected for baseline spectrum) and retention times of eluting peaks (with peak purity better than purity threshold value) were compared with those of commercially available flavonoid standards. Dose-response curves for quercetin, naringenin and kaempferol (0 to 25 μg/ml) were established to permit quantitation in the hydrolysed tomato extracts. Quercetin and kaempferol aglycones were detected and calculated from their absorbance at 370 nm and naringenin at 280 nm. Flavonol-glycosides and naringenin-chalcone were detected at 370 nm (see also Table 2). Flavonoid levels in tomatoes were calculated on a dry weight (μg/gD.wt.) basis (for peel and flesh tissues). With the HPLC system and software used, the lowest detection limit for flavonoids in tomato extracts was about 0.1 μg/ml, corresponding with ~5 μg/g dry weight. Variation between replicate injections was less than 5%.

Example 7

Characterisation of the Flavonoid Content of Non-transformed Tomato Fruit

The chromatograms from HPLC analysis of hydrolysed extracts from red fruit of variety FM6203 are shown in FIG. 3. FIG. 3A shows that both quercetin and kaespferol were present in peel tissue. By contrast, FIG. 3B shows that hydrolysed extracts from pericarp tissue from the same fruit contained only trace amounts of quercetin with no detectable levels of kaespferol. Chromatograms obtained at 280 nm (not shown) from the same extracts showed a significant accumulation of naringenin in peel, but not in the pericarp tissues.

Analysis of non-hydrolysed peel extracts showed that at least five different flavonol-glycosides and naringenin chalcone were detected (FIG. 3C). NMR-studies proved that the peak at RT=19.2 min was rutin while the peak at 17.6 min was a quercetin-3-trisaccharide: rutin with apiose linked to the glucose of the rutinoside. The retention time and absorbance spectrum of the minor peak at 19.7 min corresponded with those of quercetin-3-glucoside, while those of the peak at 21.9 min corresponded with kaempferol-3-rutinoside. The small peak at 25.6 min had an absorbance spectrum comparable to kaempferol-3-rutinoside, but its higher RT value indicates a yet unknown kaempferol-glycoside. The large peak at 34.8 min was naringenin chalcone. Aglycones of quercetin, kaempferol and naringenin (present in hydrolysed peel extracts) were not detectable in any of the non-hydrolysed extracts.

By contrast, analysis of non-hydrolysed extracts from pericarp tissue (FIG. 3D) show that this tissue only accumulates low levels of rutin.

By comparing the levels of flavonoids detected in hydrolysed extracts with those from non-hydrolysed extracts of the same tissue, we conclude that the presence of quercetin and kaempferol aglycones represent hydrolysis products of their respective glycosides.

These HPLC-analyses of flavonoid accumulation show that the flavonoid biosynthetic pathway is active in the peel but not, or to a very limited level only, in the pericarp tissue of red FM6203 tomato fruit. This conclusion was supported by mRNA analyses of important enzymes of flavonoid biosynthesis (for example chs and fls) from peel and flesh tissues (Example 3).

Example 8

Flavonoids in Peel and Flesh from Fruit Harbouring pBBC60

To determine whether the pBBC60 construct was able to modify flavonoid accumulation in tomato fruit, the flavonoid profile of red fruit from pBBC60 and pSJ89 (control) transformants was determined. This analysis was performed by HPLC using hydrolysed extracts from thirty-three pBBC60 and five pSJ89 transformed fruit.

Comparison with hydrolysed extracts from red fruit from tomato variety FM6203, transformed with either pBBC60 or pSJ89, indicated that a number of pBBC60 lines accumulated increased levels of naringenin in peel and pericarp tissues. By contrast, the levels of quercetin and kaempferol accumulation in both tissues were similar between pBBC60 and pSJ89 transformants.

Further, hydrolysed extracts of pericarp tissue from pBBC60 transformants show a range of naringenin concentrations, with one line (plant H71) expressing a 5–7 fold increase compared to pSJ89 transformed control lines. This variation in the level of naringenin accumulation from control levels to up to a 7-fold increase is believed to be representative of a transgenic population.

Three pBBC60-transformed lines that accumulated increased levels of naringenin in both peel and pericarp tissue were selected and used to generate a $T_1$ population. In addition, a corresponding $T_1$ population from pSJ89 and FM6203 was also generated to provide control fruit for comparison.

Fruits from eighteen $T_1$-generation plants were analysed to characterise their level of flavonoid accumulation. Analysis of non-hydrolysed extracts from peel tissues showed a slight increase in the level naringenin chalcone in pBBC60 transformed fruit compared to pSJ89 (control) fruit. By contrast, analysis of non-hydrolysed extracts from pericarp tissues showed that pBBC60 transformed fruit accumulate significantly higher levels of a number of naringenin glycoside type flavanones (Table 3), in particular naringenin-7-glucoside (FIG. 4A) when compared to pSJ89 controls.

The average levels of naringenin-7-glucoside in pericarp tissue from three control fruit was ~5 µg/gDW, compared to 220 µg/gDW in pBBC60 fruit number H104/5 (Table 3). These values represent an up to 44-fold increase in naringenin-7-glucoside accumulation in pericarp tissue from pBBC60 fruit relative to control values.

Furthermore, analysis of non-hydrolysed extracts from the columella tissue of pBBC60 transformed fruit also showed significant increases in the levels of a number of naringenin-glycoside type flavanones (Table 4), in particular naringenin-7-glucoside, when compared to pSJ89 control fruit (FIG. 4B). Notably, the average level of naringenin-7-glucoside in columella tissue from control fruit was ~5 µg/gDW, compared to 280 µg/gDW in pBBC60 fruit number H104/6 (Table 4). These values represent an up to 56-fold increase in naringenin-7-glucoside accumulation in columella tissue from pBBC60 fruit relative to control values.

These results show that pBBC60-transformed lines accumulate significantly increased levels of flavanone compounds in their flesh tissue relative to pSJ89 transformants. The variation in the concentration of naringenin and quercetin glycosides measured from pBBC60-transformed plants reflects a typical transgenic population. However, the data clearly show an increase in the level of naringenin glycosides, and more particularly naringenin-7-glucoside, in the flesh of pBBC60 transformed tomato fruit.

Further, it is noted that the levels of accumulation of the naringenin glycosides were significantly higher in the columella tissue when compared with the levels accumulated in the pericarp tissue.

Example 9

Flavonoids in Peel and Flesh from Fruit Harbouring pBBC80

To determine whether the pBBC80 construct was able to modify flavonoid accumulation in tomato fruit the flavonoid profile of fruit from pBBC80 and pSJ89 (control) transformants was determined. This analysis was performed by HPLC using hydrolysed extracts from thirty-four pBBC80 and eight pSJ89 transformed fruit.

Comparison between hydrolysed peel extracts from red fruit of variety FM6203, transformed with either pBBC80 or pSJ89, indicated that the mean level of naringenin accumulation was similar (FIG. 5A). However, the average levels of naringenin in peel tissue from eight control fruit was 621 µg/gDW, compared to 2425 µg/gDW in fruit from pBBC80 number F61 (Table 5). These values represent an up to 4-fold increase in naringenin accumulation in peel tissue from pBBC80 fruit relative to control values. By contrast, the levels of quercetin and kaempferol accumulation were similar between pBBC80 and pSJ89 transformants.

By contrast, in hydrolysed extracts of flesh tissue from these fruits no increase in naringenin accumulation was observed in pBBC80 transformants. Furthermore, no significant changes in the levels of quercetin and kaempferol accumulation in the flesh were observed between pBBC80 and pSJ89 transformants.

The variation in the level of accumulation of naringenin from BBC80 transformants reflects a typical transgenic population. However, the data clearly show an increase in the level of naringenin in the peel of pBBC80 transformed plants.

Example 10

Crossing pBBC60 and pBBC80 Transformed Tomato Lines

Tomato plants are functionally cleistogamous. For crossing of pBBC60 (CHS104) and pBBC80 (FLS50) transformed tomato plants, 'pollen-recipient' flowers were selected when at an immature developmental stage (tightly closed pale yellow petals). At this stage of floral development, the stamens have not elongated and so self-pollination, by pollen spreading onto the stigma is not possible. Crossing was achieved by removing the petals from these immature flowers to expose the stigma. Pollen from fully developed 'pollen-donor' flowers (open, bright yellow-flowers) was collected using fine tweezers and transferred to the-exposed stigma from the 'pollen-recipient' flower.

Following cross-pollination, flowers were labelled and the specific fruit harvested at red ripe stage. Seed was collected from these fruit and prepared for sowing by soaking in 2% HCl for 1 hour, before rinsing under running water and drying on filter paper. Dry seed stocks were stored at 4° C. prior to planting.

For identification of progeny harbouring both pBBC60 and pBBC80 transgenes, twenty seeds from each cross were germinated in compost. Leaf material was harvested from individual seedlings and total genomic DNA isolated. The presence of both the pBBC60 and pBBC80 transgenes was confirmed by PCR amplification using specific primers for each of the CHS (CHSs1 and NosAs) and FLS (FLSs1 and FLSas1) transgenes. Seedlings harbouring both CHS and FLS transgenes were selected for transfer to hydroponic culture in a glasshouse with a 16 h photoperiod and a 21/17° C. day/night temperature. Staged (18–2 dpa) red fruit were harvested for analysis.

Example 11

Flavonoids in Peel and Flesh from Fruit Harbouring Both pBBC60 and pBBC80

To determine whether concomitant expression of CHS (pBBC60) and FLS (pBBC80) was able to modify flavonoid accumulation in tomato fruit, the flavonoid profile of red fruit harbouring both pBBC60 and pBBC80 was determined. This analysis was performed by HPLC using hydrolysed extracts from four pBBC60–pBBC80 and five pSJ89 transformed fruit.

Comparison between hydrolysed peel extracts from red fruit of variety FM6203 harbouring either both CHS (pBBC60) and FLS (pBBC80) or GUS (pSJ89) transgenes indicated a number of the CHS×FLS (pBBC60+pBBC80) fruit accumulated increased levels of naringenin when compared to control pSJ89 fruit (Table 6A). The average levels of naringenin type compounds in peel tissue from four control fruit was 557 µg/gDW, compared to 2224 µg/gDW in fruit from CHSxFLS (pBBC60+pBBC80) line number 11c. These values represent an up to 4-fold increase in naringenin accumulation in peel tissue from CHS×FLS (pBBC60+pBBC80) fruit relative to control values. By contrast, the levels of quercetin and kaempferol accumulation were similar between CHS×FLS (pBBC60+pBBC80) peel extracts from fruit and pSJ89 transformants (Table 6A).

Analysis of hydrolysed extracts from pericarp tissue from these fruits showed that a number of CHS×FLS (pBBC60+ pBBC80) fruit accumulated increased levels of both naringenin and kaempferol when compared with pSJ89 control fruit (Table 6B, FIG. 6).

The average levels of naringenin and kaempferol in pericarp tissues from four control fruit was ~1 and 10 µg/gDW, compared to levels of 294 and 145 µg/gDW respectively in fruit from CHS×FLS (pBBC60+pBBC80) line number 11c (Table 6B). These values represent an up to 290- and 14-fold increase in naringenin and kaempferol accumulation respectively in pericarp tissue from CHS×FLS (pBBC60+pBBC80) fruit relative to control values.

Furthermore, analysis of columella tissue from CHS×FLS (pBBC60+pBBC80) fruits showed a further significant increase in the level of accumulation of both naringenin (up to 730-fold) and kaempferol (up to 32-fold)(Table 6C, FIG. 7). The average levels of naringenin and kaempferol accumulation in columella tissues from four control fruit was 1 and 9.3 µg/gDW, compared to levels of 727 and 299 µg/gDW respectively in fruit from CHS×FLS (pBBC60+ pBBC80) number 11c. These values represent an up to 730- and 32-fold increase in naringenin and kaempferol accumulation respectively in columella tissues from CHS×FLS (pBBC60+pBBC80) fruit relative to control values.

Analysis of non-hydrolysed pericarp and columella tissues from CHS×FLS (pBBC60+pBBC80) transformed fruit showed that the predominant naringenin and kaempferol glycosides accumulating were naringenin-7-glucoside and kaempferol-3-O-rutinoside-7-0-glucoside respectively.

These results indicate that the flavonoid biosynthetic pathway in transgenic plants is not restricted to the peel, as it is in untransformed plants, but also active in the flesh (pericarp and columella) tissues of the fruit.

Example 12

Flavonoids in Peel and Flesh from Fruit Harbouring CHS-CHI-F3H-FLS (pBBC800) Four Gene Construct To determine whether the concomitant expression of CHS-CHI-F3H-FLS (pBBC800 construct) was able to modify flavonoid accumulation in tomato fruit, the flavonoid profile from red fruit harbouring pBBC800 was determined. This analysis was performed by HPLC using non-hydrolysed extracts from thirty-two pBBC800 and ten pCJ102 (d35S-GUS-nos) transformed fruit.

Comparison between non-hydrolysed peel extracts from red fruit of variety FM6203 harbouring either CHS-CHI-F3H-FLS (pBBC800) or GUS (pCJ102) transgenes showed that a number of pBBC800 fruit accumulated increased levels of quercetin glycosides, rutin and isoquercitrin, and kaempferol glycosides, kaempferol-3-rutinoside, compared to control (pCJ102) values (Table 7, FIG. 8). The average levels of rutin and isoquercitrin in peel from ten control fruit was 773 and 13 µg/gDW, compared to levels of 31630 and 5410 µg/gDW respectively in fruit from pBBC800 transformant number 143. Similarly, the average level of accumulation of kaempferol-3-rutinoside in peel from ten control fruit was 59 µg/gDW, compared to levels of 3050 µg/gDW in fruit from pBBC800 transformant number 126. These values represent an up to 41- and 51-fold increase in quercetin and kaempferol glycoside accumulation respectively in peel tissue from pBBC800 transformed fruit relative to control values.

In addition, analysis of non-hydrolysed extracts from columella tissue revealed significant increases in the levels of a number of naringenin and kaempferol type glycosides compared to the control (pCJ102) control fruit (Table 8, FIG. 9). The average level of kaempferol-3-O-rutinoside-7-O-glucoside and naringenin-7-glucoside accumulation in columella tissue from ten control plants was 5 and 7.5 µg/gDW, compared to levels of 390 and 420 µg/gDW respectively in the pBBC800 transformant number 20. This represents up to a 78-fold and 56-fold increase in kaempferol-3-O-rutinoside-7-O-glucoside and naringenin-7-glucoside accumulation respectively, in pBBC800 transformed fruit relative to control values.

Furthermore, analysis of both peel and columella tissues from selected 'single-copy' $T_1$ fruit showed that these increases in flavonol glycosides are both heritable and stable.

These results indicate that the flavonoid biosynthetic pathway in transgenic plants is not restricted to the peel, as it is in untransformed plants, but also active in the flesh (pericarp and columella) tissues of the fruit.

Example 13

Flavonoids in Peel and Flesh from Fruit Harbouring pBBC60, pBBC80 and pBBC50

We have shown that ectopic expression of chalcone isomerase (pBBC50, FIG. 2f) significantly increases flavonol (quercetin-and kaempferol-glycosides) accumulation in tomato peel tissue (Bovy et al., WO0004175). To determine whether concomitant expression of CHS (pBBC60), FLS (pBBC80) and CHI (pBBC50) was able to modify flavonoid accumulation in tomato fruit (peel and flesh tissues), fruit harbouring pBBC60, pBBC80 and pBEC50 transgenes were generated by crossing.

Tomato plants are functionally cleistogamous. Therefore for crossing of pBBC60+pBBC80 (Example 11) with pBBC50 transformed tomato plants, 'pollen-recipient' flowers were selected when at an immature developmental, stage (tightly closed pale yellow petals). At this stage of floral development, the stamens have not elongated and so self-pollination, by pollen spreading onto the stigma is not possible. Crossing was achieved by removing the petals from these immature flowers to expose the stigma. Pollen from fully developed 'pollen-donor' flowers (open, bright yellow flowers) was collected and transferred to the exposed stigma from the 'pollen-recipient' flower.

Following cross-pollination, flowers were labelled and the specific fruit harvested at red ripe stage. Seed was collected from these fruit and prepared for sowing by soaking in 2% HCl for 1 hour, before rinsing under running water and drying on filter paper. Dry seed stocks were stored at 40° C. prior to planting.

For identification of progeny harbouring pBBC60, pBBC80 and pBBC50 transgenes, forty-five seeds were germinated in compost. Leaf material was harvested from individual seedlings and total genomic DNA isolated. The presence of the pBBC60, pBBC80 and pBBC50 transgenes was confirmed by PCR amplification using specific primers for each of the CHS (CHSs1 and NosAs), FLS (FLSs1 and FLSas1) and CHI (CHI6 and 30035S) transgenes. Seedlings harbouring CHS, FLS and CHI transgenes were selected for transfer to hydroponic culture in a glasshouse with a 16 h photoperiod and a 21/17° C. day/night temperature. Staged (18–21 dpa) red fruit were harvested for analysis.

The flavonoid profile of peel and columella tissue from red fruit harbouring pBBC60, pBBC80 and pBBC50 transgenes was determined. This analysis was performed by HPLC using non-hydrolysed extracts from 2 independent fruit selected from each of 10 pBBC60+pBBC80+pBBC50 transgenic and 4 azygous control plants.

Comparison between non-hydrolysed peel extracts from red fruit of variety FM6203 harbouring CHS (pBBC60), FLS (pBBC80) and CHI (pBBC50) transgenes and an azygous control indicated a number of the CHS×FLS×CHI (pBBC60+pBBC80+pBBC50) fruit accumulated increased levels of quercetin-glycosides, rutin and isoquercitrin, and kaempferol-glycosides, kaempferol-3-O-rutinoside (K-3-R) and kaempferol-3-O-rutinoside-7-O-glucoside (K-3-R-7-G) (Table 9). For example, the average levels of rutin and isoquercitrin in peel tissue from 8 control fruit was 2394 and 29 μg/gDW respectively, compared to levels of 64985 and 24617 μg/gDW respectively in fruit from CHS×FLS×CHI (pBBC60+pBBC80+pBBC50) line number 22.

Similarly, the average level of accumulation of kaempferol-3-O-rutinoside in peel from 8 control fruit was 276 μg/gDW, compared to levels of 3918 μg/gDW in fruit from CHS×FLS×CHI (pBBC60+pBBC80+pBBC50) line number 28.

These values represent an up to 27-, 848- and 14-fold increase in rutin, isoquercitrin and kaempferol-3-O-rutinoside accumulation respectively in peel tissue from CHS×FLS×CHI (pBBC60+pBBC80+pBBC50) transformed fruit relative to control values.

In addition, analysis of non-hydrolysed extracts from columella tissue revealed significant increases in the levels of a number of naringenin- and kaempferol-glycosides compared to the azygous control fruit (Table 10). The level of kaempferol-3-O-rutinoside-7-O-glucoside and naringenin-7-O-glucoside accumulation in columella tissue from eight control plants was ≦5 μg/gDW, compared to levels of 475 and 841 μg/gDW respectively in CHS×FLS×CHI (pBBC60+pBBC80+pBBC50) line numbers 40 and 45 respectively. As such, these values represent at least a 95-fold and 168-fold increase in kaempferol-3-O-rutinoside-7-O-glucoside and naringenin-7-O-glucoside accumulation respectively, in CHS×FLS×CHI (pBBC60+pBBC80+pBBC50) transformed fruit relative to control values.

These results indicate that the flavonoid biosynthetic pathway in CHS×FLS×CHI (pBBC60+pBBC80+pBBC50) transgenic plants is not restricted to the peel, as it is in untransformed plants, but also active in the flesh (pericarp and columella) tissues of the fruit.

Example 14

Preparation of Tomato Paste

Harvest

Firm red-ripe tomato fruit (approx. 50 kg/run) were harvested and collected in buckets up to 16 hr before processing. Fruit were rinsed in water and damaged fruit and leaves removed prior to processing. No attempt was made to standardise fruit maturity or size.

Processing Conditions

Fruit was chopped and held at the target 'break' temperature of 96° C. for 5 minutes. The chopped fruit was pulped and the resulting material passed through a 1.5 mm (0.060 in) screen. This puree was reduced to approximately 14 BRIX using a Simulated Double Effect Evaporator at 150–180° C., under vacuum at 22–23" Hg. Evaporation was continued at 12" Hg until a final BRIX of 20–25 was achieved. The resulting paste was canned in 250 g tins, sterilised in a boiling kettle for 45 min and finally cooled under a water spray for 30 min.

TABLE 1

Overview of PCR primers and adapters used.

| Seq. ID No. | Primer (*) | Sequence (5' to 3') |
|---|---|---|
| 9 | AB13 | CCCATCGATGCGTCTAGTAACATAGATGAC |
| 10 | CHSs1 | CAATTCCAGGAGTCGAGAGG |
| 11 | 167 | AGTCCCCCATGGTACGTCCTGTAGAAACC |
| 12 | 168 | CGTTTTCGTCGGTAATCACCATTCC |
| 13 | E851 | GAATTCAAGCTTGACATCCCTAAT |
| 14 | E8A2 | CTTTTGCACTGTGAATGATTAGA |
| 15 | F1 | TCGACCATATCGATGCATG |
| 16 | F2 | CATCGATATGG |
| 17 | F3 | TAAGCGGCCGCAGATCTGG |
| 18 | F4 | AATTCCAGATCTGCGGCCGCTTAAT |
| 19 | F5 | TAAGGGGTACCACCATCGATACCGAATTCTACATGCATGCATGGAGATCTCCCAAGCTTCTAAGATGCGGCCGCTAAACATGG |
| 20 | F6 | CGCGCCATGTTTAGCGGCCGCATCTTAGAAGCTTGGGAGATCTCCATGCATGTAGAATTCGGTATCGATGGTGGTACCCCTTAAT |
| 21 | F7 | AATTGCACCGGTCG |
| 22 | F8 | GATCCGACCG |
| 23 | F9 | TAGCCATGGG |
| 24 | F10 | TCGACCCATGGCTAAT |
| 25 | F12 | CCCGTCGACTTTCCCCGATCGTTCAAACATTTGGC |
| 26 | F13 | CCCGGATCCAAAAATGGTGACAGTCGAGG |
| 27 | F14 | CCGGTCGACGCAAATACATTCATGGCAAACG |
| 28 | F15 | GGCGGATCCAAAAATGTCTCCTCCAGTGTC |
| 29 | F16 | CCCGTCGACCTAAACTAGACTCCAATCACT |
| 30 | F20 | CGGGGATCCAGAGGGCCTAACTTCTGTATAGAC |
| 31 | F21 | CCCGTCGACTCGCGAAGATATAGCTAATCGC |
| 32 | F23 | CCGGGATCCGGTCTTTTGCACTGTGAATG |
| 33 | F26 | GGCGGTACCCTAATGATATTGTTCACG |
| 34 | F38 | AATTGGGCGCGCCAAGCTTCCGAATTCTTAATTAAG |
| 35 | F39 | AGCTCTTAATTAAGAATTCGGAAGCTTGGCGCGCCC |
| 36 | F48 | TGTCTCTAGCCATCTACAGG |
| 37 | F51 | GAGTTCACCACTGCTTGATGA |
| 38 | F75 | CCGGTCGACTTCGAGTATTATGGCATTGG |
| 39 | FLSs1 | AATGATAGAGGCAGCTGGTG |
| 40 | FLSas1 | GGCCTCACTAAGCAGCTTAGG |

TABLE 1-continued

Overview of PCR primers and adapters used.

| Seq. ID No. | Primer (*) | Sequence (5' to 3') |
|---|---|---|
| 41 | Gus2 | GCATCACGCAGTTCAACGCTG |
| 42 | NosAs | CCGGCAACAGGATTCAATCTT |
| 43 | 300 35S | CGCAAGACCCTTCCTCTATATAAG |
| 44 | M13 rev | AGCGGATAACAATTTCACACAGGA |
| 45 | CH16 | CTTCTCCGAGTACTGCTTGCC |

* Adapters are made by combining two primers, heating to 95° C. for 5 min and anneal both primers by cooling slowly to room temperature.

TABLE 2

Typical retention times of some flavonoid standards.

| Flavonoid standard | detection wavelength (nm) | retention time (minutes) isocratic run | gradient run |
|---|---|---|---|
| Rutin | 370 | — | 12.4 |
| Quercetin-3-glucoside | 370 | — | 13.5 |
| Kaempferol-3-rutinoside | 370 | — | 14.9 |
| Naringenin-7-glucoside | 280 | x | 17.0 |
| Quercetin | 370 | 5.1 | 26.5 |
| Naringenin | 280 | 8.3 | 35.6 |
| Naringenin chalcone | 370 | — | 38.2 |
| Kaempferol | 370 | 9.8 | 40.3 |

TABLE 3

Flavonoid levels (µg/g DW), determined by HPLC following extraction under non-hydrolysing conditions, from pericarp flesh tissue of pBBC60 (H series) and pSJ89 transformed tomato fruit.

| Line number | Narin-gly. #1 | Narin-gly #2 | Narin-7-gluc | Narin #2 | Narin #3 | Narin #4 | Narin #5 |
|---|---|---|---|---|---|---|---|
| SJ89/3(1) | <5 | 10 | <5 | 10 | <5 | 5 | <5 |
| SJ89/3(2) | <5 | <5 | <5 | 30 | <5 | <5 | <5 |
| FM6203/1 | <5 | <5 | <5 | 40 | 5 | 10 | 15 |
| H71/1 | 10 | 10 | 130 | <5 | <5 | 50 | 10 |
| H71/4 | 10 | 10 | 130 | 40 | <5 | 10 | 10 |
| H71/5 | 5 | 10 | 80 | 50 | <5 | 40 | <5 |
| H71/7 | 10 | 20 | 90 | 40 | <5 | 30 | 5 |
| H103/1 | 20 | <5 | 190 | <5 | <5 | 50 | 10 |
| H103/2 | <5 | 5 | 40 | 5 | <5 | 20 | 5 |
| H103/3 | 5 | 10 | 70 | 20 | <5 | 30 | <5 |
| H103/4 | 20 | 30 | 180 | 30 | <5 | 60 | 10 |
| H103/5 | 5 | 20 | 90 | 50 | <5 | <5 | 10 |
| H104/1 | 20 | 20 | 160 | 20 | <5 | 60 | 10 |
| H104/5 | 40 | 50 | 220 | 30 | <5 | 90 | 20 |
| H104/6 | 10 | 10 | 60 | 5 | <5 | 30 | 5 |

(narin = narigenin, gly = glycoside)

TABLE 4

Flavonoid levels (µg/g DW), determined by HPLC following extraction under hydrolysing conditions, from columella tissue of pBBC60 (H series) and pSJ89 transformed tomato fruit.

| Line number | Narin-gly. #1 | Narin-gly #2 | narin-7-gluc | Narin #2 | Narin #3 | Narin #4 | Narin #5 |
|---|---|---|---|---|---|---|---|
| SJ89/3(3) | <5 | <5 | <5 | 30 | <5 | 10 | <5 |
| H71/1 | 20 | 10 | 230 | 50 | 30 | 100 | 30 |
| H71/2 | 20 | 10 | 110 | 20 | <5 | 10 | 5 |
| H71/4 | 20 | 20 | 170 | 20 | <5 | 50 | 10 |
| H71/5 | 10 | 10 | 80 | 50 | <5 | 40 | 5 |
| H71/7 | 20 | 20 | 200 | 40 | 10 | 60 | 20 |
| H104/2 | <5 | 20 | 180 | 20 | <5 | 70 | 20 |
| H104/3 | 70 | 40 | 230 | 50 | 30 | 100 | 30 |
| H104/5 | 20 | 20 | 200 | 20 | <5 | 80 | 20 |
| H104/6 | 100 | 60 | 280 | 20 | <5 | 110 | 30 |

(narin = narigenin, gly = glycoside)

TABLE 5

Flavonoid levels µg/gDwt, determined by HPLC following extrcation under hydrolysing conditions from peel tissues from pBBC80 (F series) and pSJ89 (EG series) transformed tomato fruit.

| Line Number | Naringenin | Quercetin | Kaempferol |
|---|---|---|---|
| EG68 | 168 | 142 | 23 |
| EG73 | 260 | 210 | 30 |
| EG72 | 310 | 175 | 25 |
| EG69 | 380 | 235 | 15 |
| EG71 | 695 | 285 | 40 |
| EG3 | 840 | 350 | 55 |
| EG1 | 1049 | 241 | 20 |
| EG74 | 1268 | 359 | 34 |
| F101 | 80 | 120 | 5 |
| F51 | 160 | 235 | 40 |
| E50 | 175 | 105 | 30 |
| F96 | 185 | 180 | 30 |
| F94 | 200 | 135 | 20 |
| F105 | 220 | 200 | 30 |
| F27 | 267 | 191 | 20 |
| F88 | 285 | 80 | 20 |
| F92 | 335 | 330 | 25 |
| F24 | 337 | 162 | 17 |
| F28 | 345 | 230 | 20 |
| F90 | 355 | 165 | 25 |
| F23 | 410 | 265 | 45 |
| F121 | 470 | 330 | 50 |
| F97 | 510 | 345 | 65 |
| F89 | 525 | 270 | 35 |
| F12 | 540 | 340 | 50 |
| F109 | 565 | 165 | 30 |
| F80 | 565 | 310 | 35 |
| F104 | 635 | 130 | 20 |
| F99 | 649 | 207 | 25 |
| F57 | 654 | 143 | 12 |
| F21 | 704 | 248 | 23 |
| F13 | 815 | 285 | 45 |
| F53 | 835 | 264 | 20 |
| F31 | 1126 | 272 | 30 |
| F93 | 11200 | 350 | 80 |
| F1 | 11305 | 380 | 45 |
| F98 | 1455 | 385 | 50 |
| F60 | 1830 | 440 | 90 |
| F85 | 1990 | 470 | 80 |
| F63 | 2040 | 520 | 70 |
| F61 | 2425 | 585 | 105 |

TABLE 6

Flavonoid levels μg/gDwt, determined by HPLC following extraction under hydrolysing conditions from peel (A), pericarp (B) and columella (C) tissues from tomato fruit harbouring both CHS and FLS (CHSxFLS series) or GUS control (SJ89 series) transgenes.

|  | Naringenin | Quercetin | Kaempferol |
|---|---|---|---|
| A. Peel | | | |
| SJ89/1 | 450 | 639 | 32 |
| SJ89/2 | 525 | 471 | 58 |
| SJ89/3 | 622 | 476 | 34 |
| SJ89/4 | 605 | 597 | 53 |
| SJ89/5 | 582 | 546 | 50 |
| CHSxFLS/6 | 316 | 344 | 45 |
| CHSxFLS/8 | 588 | 446 | 67 |
| CHSxFLS/10 | 976 | 705 | 112 |
| CHSxFLS/11 | 2224 | 807 | 108 |
| B. Pericarp | | | |
| SJ89/1 | 1 | 6 | 9 |
| SJ89/2 | 1 | 6 | 11 |
| SJ89/3 | 1 | 10 | 11 |
| SJ89/4 | 1 | 6 | 8 |
| SJ89/5 | 1 | 2 | 11 |
| CHSxFLS/6 | 1 | 5 | 9 |
| CHSxFLS/8 | 69 | 19 | 72 |
| CHSxFLS/10 | 189 | 23 | 108 |
| CHSxFLS/11 | 294 | 31 | 145 |
| C. Columella | | | |
| SJ89/1 | 1 | 8 | 8 |
| SJ89/2 | 1 | 6 | 9 |
| SJ89/3 | 1 | 4 | 11 |
| SJ89/4 | 1 | 10 | 9 |
| SJ89/5 | 1 | 11 | 10 |
| CHSxFLS/6 | <1 | 5 | 8 |
| CHSxFLS/8 | 317 | 23 | 238 |
| CHSxFLS/10 | 673 | 19 | 266 |
| CHSxFLS/11 | 727 | 18 | 299 |

TABLE 7

Flavonoid levels (μg/gDwt), determined by HPLC following extraction under non-hydrolysing conditions from peel tissue from pBBC800 and pCJ102 transformed tomato fruit.

| pBBC800 Line nos. | quer-gly. #1 | kaemp-gly. #1 | quer-trisac. | rutin | iso-quercitrin | k-3-rut. | quer-gly. #2 | Kaemp-gly. #3 | Kaemp-gly. #2 | naringenin chalcone |
|---|---|---|---|---|---|---|---|---|---|---|
| 2 | 520 | 130 | 210 | 20920 | 3150 | 1130 | 780 | 160 | 90 | 20 |
| 3 | 40 | <5 | 60 | 370 | <5 | 20 | <5 | <5 | 20 | 100 |
| 7 | 220 | 50 | 150 | 8200 | 1863 | 320 | 350 | 60 | 20 | 20 |
| 15 | 430 | 40 | 170 | 7370 | 130 | 120 | 230 | 10 | 30 | 10 |
| 20 | 1740 | 10 | 650 | 12050 | 90 | 30 | 160 | 10 | 20 | 40 |
| 22 | 530 | 30 | 590 | 22410 | 4640 | 240 | 1530 | 60 | 30 | 30 |
| 33 | 3290 | 30 | 530 | 21780 | 170 | 20 | 1070 | 20 | 20 | 30 |
| 34 | 610 | 30 | 500 | 20100 | 1930 | 230 | 490 | 30 | 40 | 20 |
| 37 | 660 | 50 | 190 | 1570 | 370 | 230 | 400 | <5 | 10 | 5 |
| 41 | 430 | 60 | 200 | 11040 | 1160 | 300 | 360 | 50 | 20 | 10 |
| 42 | 50 | 10 | 330 | 980 | 5 | 60 | 20 | <5 | 20 | 650 |
| 90 | 170 | 40 | 340 | 12330 | 1190 | 570 | 340 | 50 | 30 | 310 |
| 92 | 290 | 70 | 590 | 18710 | 2490 | 830 | 400 | 90 | 60 | 5 |
| 123 | 490 | 260 | 110 | 26750 | 13040 | 2020 | 3520 | 1210 | 360 | 10 |
| 125 | 720 | 100 | 130 | 11370 | 430 | 250 | 270 | 40 | 30 | <5 |
| 145 | 670 | 200 | 290 | 23930 | 9170 | 1450 | 210 | 650 | 210 | <5 |
| 111 | 580 | 120 | 140 | 13440 | 2250 | 620 | 40 | 180 | 40 | 30 |
| 112 | 570 | 80 | 330 | 24090 | 5030 | 750 | 1210 | 230 | 70 | 20 |
| 114 | 1380 | 20 | 300 | 9930 | 240 | 80 | 450 | <5 | 30 | 20 |
| 115 | 570 | 90 | 330 | 17060 | 2260 | 650 | 840 | 140 | 70 | 20 |
| 117 | 60 | 10 | 180 | 870 | 10 | 50 | 10 | 10 | <5 | 1160 |
| 118 | 1380 | 140 | 520 | 40750 | 10010 | 1260 | 2090 | 410 | 120 | 60 |
| 120 | 1300 | 30 | 210 | 5440 | 80 | 30 | 150 | <5 | 30 | 10 |
| 126 | 1060 | 380 | 140 | 27170 | 6420 | 3050 | 1200 | 1150 | 280 | 10 |
| 128 | 660 | 110 | 190 | 4970 | 220 | 60 | 300 | 20 | <5 | <5 |

TABLE 7-continued

Flavonoid levels (μg/gDwt), determined by HPLC following extraction under non-hydrolysing conditions from peel tissue from pBBC800 and pCJ102 transformed tomato fruit.

| 131 | 1490 | 50 | 430 | 9810 | 180 | 50 | 290 | <5 | 10 | 10 |
|---|---|---|---|---|---|---|---|---|---|---|
| 135 | 650 | 100 | 380 | 23260 | 3170 | 890 | 700 | 160 | 80 | 10 |
| 135 | 820 | 150 | 340 | 22470 | 2800 | 980 | 810 | 160 | 80 | 10 |
| 143 | 1060 | 90 | 330 | 31630 | 5410 | 640 | 940 | 150 | 30 | 20 |
| 149 | 1190 | 90 | 440 | 23300 | 460 | 500 | 220 | 10 | 20 | 10 |
| 154 | 510 | 40 | 190 | 7600 | 130 | 50 | 210 | 10 | 120 | 10 |
| 155 | 330 | 90 | 210 | 8720 | 2300 | 450 | 420 | 170 | 140 | 10 |

| pCJ102 Line nos. | quer-gly. #1 | Kaemp-gly. #1 | quer-trisac. | rutin | iso-quercitrin | k-3-rut. | quer-gly #2 | Kaemp-gly. #3 | Kaemp-gly. #2 | Naringenin chalcone |
|---|---|---|---|---|---|---|---|---|---|---|
| 1 | 200 | 20 | 300 | 1350 | 30 | 70 | 40 | 20 | 10 | 870 |
| 2 | 80 | 10 | 210 | 1060 | 10 | 80 | 10 | 10 | 10 | 880 |
| 3 | 80 | 10 | 170 | 920 | 30 | 40 | 20 | 10 | 5 | 690 |
| 4 | 130 | 30 | 150 | 1020 | <5 | 110 | 10 | <5 | 40 | 360 |
| 5 | 80 | 20 | 120 | 530 | <5 | 80 | 20 | <5 | 40 | 330 |
| 6 | 80 | 10 | 80 | 570 | <5 | 50 | <5 | <5 | 40 | 260 |
| 7 | 50 | 10 | 190 | 490 | <5 | 30 | 10 | <5 | 5 | 220 |
| 8 | 90 | 10 | 100 | 600 | <5 | 60 | 10 | <5 | <5 | 320 |
| 9 | 50 | 10 | 60 | 480 | <5 | 30 | <5 | <5 | 20 | 220 |
| 10 | 60 | 10 | 260 | 710 | 30 | 40 | 10 | <5 | 10 | 120 |

TABLE 8

Flavonoid levels (μg/gDwt), determined by HPLC following extraction under non-hydrolysing conditions from columella tissue from pBBC800 and pCJ102 transformed tomato fruit.

| | quer-gly #1 | rutin | k-3-rut. | k-gly #1 | k-gly #2 | narin gly #1 | narin gly #2 | narin-7-gluc. | narin #2 | narin #3 | narin #4 | narin #5 |
|---|---|---|---|---|---|---|---|---|---|---|---|---|
| pBBC800 Line Nos. | | | | | | | | | | | | |
| 2 | 20 | 60 | 10 | 30 | <5 | 5 | 5 | 80 | <5 | <5 | 40 | <5 |
| 3 | <5 | 20 | <5 | <5 | <5 | <5 | <5 | <5 | <5 | <5 | <5 | <5 |
| 7 | 20 | 50 | 50 | 120 | 40 | 50 | 20 | 50 | <5 | <5 | 80 | <5 |
| 15 | 20 | 20 | 30 | 120 | 10 | 20 | 10 | 60 | <5 | <5 | 30 | 5 |
| 20 | 10 | 80 | 90 | 390 | 20 | 140 | 30 | 420 | <5 | <5 | 90 | 40 |
| 22 | 20 | 40 | 40 | 90 | 10 | 60 | 20 | 150 | <5 | <5 | 50 | 5 |
| 33 | 10 | 10 | 10 | 30 | <5 | 20 | 10 | 100 | <5 | <5 | 40 | 10 |
| 34 | 20 | 30 | 10 | 40 | <5 | 30 | 5 | 100 | <5 | <5 | 40 | 5 |
| 37 | 20 | 30 | 30 | 240 | 10 | 50 | 10 | 140 | <5 | <5 | 40 | 10 |
| 41 | 20 | 20 | 40 | 250 | <5 | 90 | 10 | 180 | 30 | 10 | 40 | 20 |
| 42 | <5 | 20 | <5 | <5 | <5 | <5 | <5 | 5 | <5 | 5 | <5 | <5 |
| 92 | 40 | 90 | 100 | 320 | 10 | <5 | <5 | 5 | <5 | 20 | 50 | <5 |
| 111 | 20 | 30 | 90 | 360 | 20 | 60 | 20 | 320 | <5 | 5 | 60 | 10 |
| 112 | 20 | 50 | 30 | 70 | <5 | 30 | 10 | 140 | <5 | <5 | 50 | <5 |
| 114 | <5 | 30 | <5 | 5 | <5 | 20 | 10 | 40 | <5 | 5 | 10 | <5 |
| 115 | 30 | 50 | 30 | 120 | 10 | 30 | 10 | 90 | 40 | <5 | 30 | <5 |
| 117 | <5 | 30 | <5 | <5 | <5 | <5 | <5 | 10 | <5 | <5 | <5 | <5 |
| 118 | 20 | 40 | 30 | 130 | 5 | 30 | 5 | 120 | <5 | <5 | 40 | 5 |
| 120 | 20 | 20 | 20 | 110 | <5 | 40 | 5 | 150 | <5 | 5 | 50 | 10 |
| 123 | <5 | 20 | 40 | 120 | <5 | 110 | 20 | 280 | 60 | 10 | 70 | 40 |
| 125 | 20 | 10 | 40 | 290 | 10 | 40 | 20 | 190 | <5 | <5 | 40 | 10 |
| 126 | 10 | 20 | 50 | 120 | <5 | 30 | 5 | 170 | <5 | <5 | 40 | 10 |
| 128 | 30 | 50 | 110 | 320 | 10 | 100 | 20 | 320 | <5 | 5 | 130 | 20 |
| 131 | 30 | 30 | 70 | 300 | 20 | 160 | 30 | 310 | <5 | 5 | 90 | 20 |
| 134 | 10 | 30 | 30 | 100 | <5 | <5 | <5 | 80 | <5 | <5 | 10 | <5 |
| 135 | 20 | 50 | 30 | 170 | 10 | 30 | 10 | 120 | 20 | <5 | 10 | 10 |
| 143 | 10 | 30 | 100 | 230 | 5 | 40 | 10 | 260 | <5 | 10 | 160 | 30 |
| 145 | 20 | 60 | 20 | 130 | 5 | 40 | 10 | 110 | <5 | <5 | 30 | 5 |
| 149 | 20 | 50 | 20 | 80 | <5 | 10 | 10 | 130 | <5 | 5 | 40 | <5 |
| 154 | 20 | 30 | 20 | 110 | <5 | 30 | 10 | 120 | <5 | 5 | 60 | <5 |
| 155 | 20 | 20 | 20 | 70 | 10 | 40 | 10 | 70 | <5 | <5 | 40 | <5 |

TABLE 8-continued

Flavonoid levels (µg/gDwt), determined by HPLC following extraction under non-hydrolysing conditions from columella tissue from pBBC800 and pCJ102 transformed tomato fruit.

| | quer-gly #1 | rutin | k-3-rut. | k-gly #1 | k-gly #2 | narin gly #1 | narin gly #2 | narin-7-gluc. | narin #2 | narin #3 | narin #4 | narin #5 |
|---|---|---|---|---|---|---|---|---|---|---|---|---|
| pCJ102 Line nos. | | | | | | | | | | | | |
| 1 | <5 | 20 | <5 | <5 | <5 | <5 | <5 | 10 | <5 | 5 | <5 | <5 |
| 2 | <5 | 20 | <5 | <5 | <5 | <5 | <5 | 10 | <5 | <5 | 10 | <5 |
| 3 | <5 | 10 | <5 | 5 | <5 | <5 | <5 | 5 | <5 | 5 | 5 | <5 |
| 4 | <5 | 20 | <5 | <5 | <5 | <5 | <5 | <5 | <5 | 5 | <5 | <5 |
| 5 | <5 | 10 | <5 | <5 | <5 | <5 | <5 | <5 | 10 | 5 | <5 | <5 |
| 6 | <5 | 20 | <5 | <5 | <5 | <5 | <5 | 10 | <5 | 5 | 10 | <5 |
| 7 | <5 | 50 | <5 | <5 | <5 | <5 | <5 | 10 | <5 | 5 | 10 | <5 |
| 8 | <5 | 40 | <5 | <5 | <5 | <5 | <5 | <5 | <5 | 5 | <5 | <5 |
| 9 | <5 | 20 | <5 | <5 | <5 | <5 | <5 | 10 | <5 | 5 | 10 | <5 |
| 10 | <5 | 10 | <5 | <5 | <5 | <5 | <5 | 5 | <5 | <5 | <5 | <5 |

"narin" = naringenin type compounds

TABLE 9

Flavonoid levels (µg/gDwt), determined by HPLC following extraction under non-hydrolysing conditions from peel tissue from pBBC60 + pBBC80 + pBBC50 (CHS × FLS × CHI) and C11 azygous control fruit.

| Line # | N-7-Glu | N gly #5 | N gly #6 | Rutin | Iso-quer | K-3-R-7-G | K-3-R |
|---|---|---|---|---|---|---|---|
| C11AZ2A | 45.8 | <5 | <5 | 1570 | 7.9 | 12.8 | 70.1 |
| C11AZ2B | 89.6 | <5 | <5 | 1034 | <5 | 33.1 | 106.9 |
| C11AZ3A | 689.6 | <5 | <5 | 3758 | 21.7 | 145.7 | 594.6 |
| C11AZ3B | 297.1 | <5 | <5 | 4857 | 73.2 | 56.6 | 406.8 |
| C11AZ4A | 246.1 | <5 | 73.3 | 2097 | <5 | 41.3 | 212.9 |
| C11AZ4B | 551.1 | <5 | 14.6 | 2850 | 13.4 | 12.0 | 120.9 |
| C11AZ6A | 138.9 | 29.7 | <5 | 1407.2 | 29.4 | <5 | 242.6 |
| C11AZ6B | 180.4 | 22.7 | <5 | 1508.9 | <5 | 80.5 | 287.3 |
| 10A | <5 | <5 | <5 | 48192 | 17690 | 407.3 | 3080 |
| 10B | <5 | <5 | <5 | 48340 | 16449 | 384.2 | 2565 |
| 22A | <5 | <5 | <5 | 61854 | 21377 | 285.1 | 2382 |
| 22B | <5 | <5 | <5 | 68117 | 27857 | 418.2 | 3471 |
| 28A | <5 | <5 | <5 | 51285 | 18223 | 441.6 | 3194 |
| 28B | <5 | <5 | <5 | 49689 | 9467 | 742 | 4642 |
| 37A | <5 | <5 | <5 | 45823 | 14572 | 431.1 | 2524 |
| 37B | <5 | <5 | <5 | 44348 | 16191 | 527.8 | 2903 |
| 40A | <5 | <5 | <5 | 40277 | 11980 | 237.2 | 1790 |
| 40B | <5 | <5 | <5 | 55452 | 19220 | 303.2 | 2657 |
| 42A | <5 | <5 | <5 | 57723 | 21110 | 344.6 | 2751 |
| 42B | <5 | <5 | <5 | 51570 | 15709 | 314 | 2536 |
| 43A | <5 | <5 | <5 | 44574 | 14875 | 360 | 2152 |
| 43B | <5 | <5 | <5 | 41553 | 14635 | 264.6 | 1550 |
| 44A | <5 | <5 | <5 | 50140 | 17895 | 302.2 | 2696 |
| 44B | <5 | <5 | <5 | 56067 | 16279 | 227 | 2319 |
| 45A | <5 | <5 | <5 | 48651 | 20440 | 360.6 | 2320 |
| 45B | <5 | <5 | <5 | 52471 | 21194 | 331.7 | 2315 |
| 48A | <5 | <5 | <5 | 38465 | 13760 | 218.4 | 1713 |
| 48B | <5 | <5 | <5 | 45996 | 16084 | 225.3 | 2209 |

TABLE 10

Flavonoid levels (µg/gDwt), determined by HPLC following extraction under non-hydrolysing conditions from columella tissue from pBBC60 + pBBC80 + PBBC50 (CHS × FLS × CHI) and C11 azygous control fruit.

| Line # | N-7-Glu | N gly #5 | N gly #6 | Rutin | Iso-quer | K-3-R-7-G | K-3-R |
|---|---|---|---|---|---|---|---|
| C11AZ2A | <5 | <5 | <5 | 48.7 | 6.1 | <5 | <5 |
| C11AZ2B | <5 | <5 | <5 | 41.6 | 5.8 | <5 | <5 |
| C11AZ3A | <5 | <5 | <5 | 57.6 | 9.5 | <5 | <5 |
| C11AZ3B | <5 | <5 | <5 | 25.6 | 5 | <5 | <5 |

TABLE 10-continued

Flavonoid levels (μg/gDwt), determined by HPLC following extraction under non-hydrolysing conditions from columella tissue from pBBC60 + pBBC80 + PBBC50 (CHS × FLS × CHI) and C11 azygous control fruit.

| Line # | N-7-Glu | N gly #5 | N gly #6 | Rutin | Iso-quer | K-3-R-7-G | K-3-R |
|---|---|---|---|---|---|---|---|
| C11AZ4A | <5 | <5 | 28.9 | <5 | <5 | <5 | <5 |
| C11AZ4B | <5 | <5 | <5 | 61.4 | <5 | <5 | <5 |
| C11AZ6A | <5 | <5 | <5 | 40.1 | <5 | <5 | <5 |
| C11AZ6B | <5 | <5 | <5 | 39.2 | <5 | <5 | <5 |
| 10A | 463.7 | 179.4 | 68.9 | 65.1 | <5 | 303.5 | 120 |
| 10B | 556.1 | 253.4 | 99.9 | 65.1 | 12.6 | 375.1 | 102.2 |
| 22A | 470.6 | 262.5 | 69.7 | 225.9 | 65.2 | 259.4 | 97.8 |
| 22B | 611 | 304.2 | 111.4 | 55.3 | 14 | 304 | 97.1 |
| 28A | 564.8 | 224 | 97.8 | 176.6 | 52.9 | 333.1 | 102.3 |
| 28B | 441.6 | 169.6 | 82.2 | 122.8 | 29.3 | 324.8 | 85 |
| 37A | 691 | 244.4 | 63.7 | 117.4 | 33.9 | 389.7 | 149 |
| 37B | 493.7 | 180.7 | 52.4 | 126 | 31.8 | 261.6 | 131.9 |
| 40A | 695.6 | 287.3 | 87.2 | 64.6 | 14.7 | 516.3 | 187.4 |
| 40B | 668.4 | 236.1 | 84.5 | 191 | 60.4 | 434.8 | 173.5 |
| 42A | 757.1 | 378.8 | 95.9 | 71 | n.d | 301.8 | 157.6 |
| 42B | 557 | 173.6 | 60.3 | 228.5 | 51.6 | 405.7 | 231.3 |
| 43A | 679.7 | 375 | 98.1 | 76.8 | <5 | 340.1 | 140.4 |
| 43B | 811.2 | 339.5 | 102.3 | 86.6 | <5 | 408.3 | 120.7 |
| 44A | n.d | n.d | n.d | 94.8 | 22.7 | n.d | n.d |
| 44B | n.d | n.d | n.d | 157.1 | 36.6 | n.d | n.d |
| 45A | 848.6 | 368.9 | 117.7 | 190.9 | 66.9 | 304.1 | 177.1 |
| 45B | 835.7 | 379.9 | 125.1 | 80 | 15.3 | 295.4 | 158.9 |
| 48A | n.d | n.d | n.d | 27.6 | <5 | n.d | n.d |
| 48B | n.d | n.d | n.d | 81 | <5 | n.d | n.d | n.d not determined.

The Following Literature References are Mentioned in the Examples:
Becker, D. et al., (1992). Plant Mol. Biol. 20:1195–1197.
Bovy, A. G. et al., (1995). Acta Hortic. 405:179–189.
Dente, L., and Cortese, R. (1987) Methods Enzymology 155:111–119.
Gynheung et al., (1988). in Plant Molecular Biology Manual, Eds.
Gelvin/Schilperoort, Kluwer Academic Publishers pPMAN-A311-19.
Hanahan, D. (1983). J. Mol. Biol. 166:557–580.
Hertog, M. G. L. et al., (1992). J. Agric. Food Chem. 40:1591–1598.
Hoekema, A. et al., (1985). Plant Mol. Biol. 5:85–89.
Jefferson, R. et al., (1987). EMBO J. 6:3901–3907.
Koes, R. E. et al., (1988). Plant Mol. Biol. 10:375–385.
Lloyd, A. et al., (1992). Science 258:1773–1775.
Murashige, T. and Skoog, F. (1962). Physiol. Plant. 15:73–97.
Symons et al., (1990). Biotech. 8:217–221.
Van Tunen A. J., et al., (1988). EMBO J 7:1257–1263.
Van Engelen, F. et al., (1995). Transgenic Res. 4:288–290.
Vancanneyt, G., et al., (1990). Mol. Gen. Genet. 220: 245–250.

The invention claimed is:

1. A process for increasing the flavonoid content of a plant, comprising transforming said plant with one or more nucleotide sequences encoding a chalcone synthase and one or more nucleotide sequences encoding a flavonol synthase, wherein said nucleotides sequences are operably linked to a promoter and the flavonoid content of the plant is increased.

2. A process according to claim 1 wherein said process comprises the steps;
   (i) transforming a plant cell with a gene construct;
   (ii) regenerating said plant cell to produce a transformed plant;
wherein said gene construct comprises one or more nucleotide sequences encoding a chalcone synthase and one or more nucleotide sequences encoding a flavonol synthase.

3. A process according to claim 2 wherein said one or more nucleotide sequences comprise sequences of SEQ ID NO: 1 and SEQ ID NO: 7.

4. A process according to claim 1 wherein the flavonol content of said plant is increased in leaf tissue and/or fruit tissue.

5. A process according to claim 4 wherein said increase in flavonoid content comprises an increase in flavanone content and/or an increase in flavonol content.

6. A process according to claim 5 wherein the flavanone content and/or the flavonol content of said plant is increased in pericarp tissue.

7. A process according to claim 5 wherein the flavanone content and/or flavonol content of said plant is increased in columella tissue.

8. A process according to any one of claims 5, 6 or 7 wherein said flavanone content comprises naringenin.

9. A process according to any one of claims 5, 6 or 7 wherein said flavonol content comprises kaempferol.

10. A process according to claim 1 wherein said plant is selected from a group comprising tobacco, Pisum, Brassicae, Phaseolus, Spinacea, Solanaceae, Daucus, Capsicum, Ribesiaceac, Pomaceae, Rosaceae, Rutaceae, sunflower, soybean, rape.

11. A process according to claim 10 wherein said plant is a tomato plant.

12. A process according to claim 10 wherein said plant is a pea or spinach plant.

13. A gene construct comprising one or more nucleotide sequence encoding a chalcone synthase and one or more nucleotide sequences encoding a flavonol synthase wherein said nucleotide sequences are operably linked to a promoter.

14. A gene construct according to claim 13 wherein said gene construct comprises nucleotide sequences of SEQ ID NO: 1 and SEQ ID NO: 7.

15. A transformed plant comprising the construct according to either claim 13 or claim 14.

16. A genetically modified plant with an increased flavonoid content compared to an equivalent unmodified plant, wherein said genetically modified plant is obtainable by the process according to claim 1.

17. A genetically modified plant according to claim 16 wherein said plant is selected from a group comprising tobacco, Pisum, Brassicae, Phaseolus, Spinacea, Solanaceae, Daucus, Capsicum, Ribesiaceae, Pomaceae, Rosaceae, Rutaceae, sunflower, soybean, rape.

18. A genetically modified plant according to claim 17 wherein said plant is a pea plant or a spinach plant.

19. A genetically modified plant according to claim 17 wherein said plant is a tomato plant.

* * * * *